(12) United States Patent
Scheller et al.

(10) Patent No.: US 11,234,766 B2
(45) Date of Patent: *Feb. 1, 2022

(54) STEERABLE LASER PROBE

(71) Applicant: KATALYST SURGICAL, LLC, Chesterfield, MO (US)

(72) Inventors: Gregg D. Scheller, Wildwood, MO (US); Matthew N Zeid, Ballwin, MO (US)

(73) Assignees: Gregg D Scheller, Wildwood, MO (US); Matthew N Zeid, Ballwin, MO (US)

( * ) Notice: Subject to any disclaimer, the term of this patent is extended or adjusted under 35 U.S.C. 154(b) by 109 days.

This patent is subject to a terminal disclaimer.

(21) Appl. No.: 16/385,058

(22) Filed: Apr. 16, 2019

(65) Prior Publication Data

US 2019/0239952 A1  Aug. 8, 2019

Related U.S. Application Data

(60) Division of application No. 15/377,586, filed on Dec. 13, 2016, now Pat. No. 10,307,208, which is a
(Continued)

(51) Int. Cl.
*A61B 18/22* (2006.01)
*A61F 9/008* (2006.01)
*A61B 18/00* (2006.01)

(52) U.S. Cl.
CPC .............. *A61B 18/22* (2013.01); *A61F 9/008* (2013.01); *A61F 9/00821* (2013.01);
(Continued)

(58) Field of Classification Search
CPC .......... A61B 18/22; A61B 2018/00589; A61B 2018/2238; A61B 2018/2244;
(Continued)

(56) References Cited

U.S. PATENT DOCUMENTS

| 3,174,851 A | 3/1965 | Buehler et al. |
| 4,122,853 A | 10/1978 | Smith |

(Continued)

FOREIGN PATENT DOCUMENTS

| EP | 0900547 B1 | 3/1999 |
| WO | WO 2006/091597 A1 | 8/2006 |
| WO | WO 2013/133717 | 9/2013 |

OTHER PUBLICATIONS

H. Fischer, B. Vogel, W. Pfleging, H. Besser, Flexible distal tip made of nitinol (NiTi) for a steerable endoscopic camera system, Materials Science and Engineering A273-275 (1999) 780-783.
(Continued)

*Primary Examiner* — Jonathan T Kuo
*Assistant Examiner* — Vynn V Huh

(57) ABSTRACT

A steerable laser probe may include a handle having a handle distal end and a handle proximal end, an actuation lever of the handle, a flexible housing tube having a flexible housing tube distal end and a flexible housing tube proximal end, and an optic fiber disposed within an inner bore of the handle and the flexible housing tube. An actuation of the actuation lever may gradually curve the flexible housing tube and the optic fiber. An actuation of the actuation lever may gradually straighten the flexible housing tube and the optic fiber.

5 Claims, 23 Drawing Sheets

Related U.S. Application Data continuation of application No. 13/862,433, filed on Apr. 14, 2013.

(52) U.S. Cl.
CPC ...... *A61F 9/00823* (2013.01); *A61B 2018/00589* (2013.01); *A61B 2018/225* (2013.01); *A61B 2018/2238* (2013.01); *A61B 2018/2244* (2013.01); *A61F 2009/00863* (2013.01)

(58) Field of Classification Search
CPC ......... A61B 2018/225; A61B 18/20–28; A61F 2009/00863; A61F 9/008; A61F 9/00821; A61F 9/00823; A61N 5/06–2005/073
USPC ..................................... 606/2–19; 607/88–94
See application file for complete search history.

(56) References Cited

U.S. PATENT DOCUMENTS

| | | | |
|---|---|---|---|
| 4,147,443 A | 4/1979 | Skobel | |
| 4,744,360 A | 5/1988 | Bath | |
| 5,190,050 A | 3/1993 | Nitzsche | |
| 5,228,852 A | 7/1993 | Goldsmith et al. | |
| 5,257,988 A | 11/1993 | L'Esperance, Jr. | |
| 5,322,064 A | 6/1994 | Lundquist | |
| 5,355,871 A | 10/1994 | Hurley et al. | |
| 5,381,782 A | 1/1995 | DeLaRama et al. | |
| 5,439,000 A | 8/1995 | Gunderson et al. | |
| 5,454,794 A | 10/1995 | Narciso et al. | |
| 5,520,222 A | 5/1996 | Chikama | |
| 5,735,842 A | 4/1998 | Kruege et al. | |
| 5,855,577 A | 1/1999 | Murphy-Chutorian et al. | |
| 5,873,865 A | 2/1999 | Horzewski et al. | |
| 5,951,544 A | 9/1999 | Konwitz | |
| 6,123,699 A | 9/2000 | Webster, Jr. | |
| 6,126,654 A | 10/2000 | Giba et al. | |
| 6,178,354 B1 | 1/2001 | Gibson | |
| 6,198,974 B1 | 3/2001 | Webster, Jr. | |
| 6,330,837 B1 | 12/2001 | Charles et al. | |
| 6,352,531 B1 | 3/2002 | O'Connor et al. | |
| 6,488,695 B1 | 12/2002 | Hickingbotham | |
| 6,505,530 B2 | 1/2003 | Adler et al. | |
| 6,530,913 B1 | 3/2003 | Giba et al. | |
| 6,533,772 B1 | 3/2003 | Sherts et al. | |
| 6,551,302 B1 | 4/2003 | Rosinko et al. | |
| 6,572,608 B1 | 6/2003 | Lee et al. | |
| 6,620,153 B2 | 9/2003 | Mueller et al. | |
| 6,730,076 B2 | 5/2004 | Hickingbotham | |
| 6,863,668 B2 | 3/2005 | Gillespie et al. | |
| 6,872,214 B2 | 3/2005 | Sonnenschein et al. | |
| 6,984,230 B2 | 1/2006 | Scheller et al. | |
| 7,004,957 B1 | 2/2006 | Dampney et al. | |
| 7,226,444 B1 | 6/2007 | Ellman et al. | |
| 7,303,533 B2 | 12/2007 | Johansen et al. | |
| 7,402,158 B2 | 7/2008 | Scheller et al. | |
| 7,555,327 B2 | 6/2009 | Matlock | |
| 7,632,242 B2 | 12/2009 | Griffin et al. | |
| 7,766,904 B2 | 8/2010 | McGowan, Sr. et al. | |
| 7,935,108 B2 | 5/2011 | Baxter et al. | |
| 8,038,692 B2 | 10/2011 | Valencia et al. | |
| 8,075,553 B2 | 12/2011 | Scheller et al. | |
| 8,197,468 B2 | 6/2012 | Scheller et al. | |
| 8,840,605 B2 | 9/2014 | Scheller et al. | |
| 8,840,607 B2 | 9/2014 | Scheller et al. | |
| 8,951,245 B2 | 2/2015 | Scheller et al. | |
| 8,968,277 B2 | 3/2015 | Scheller et al. | |
| 9,023,019 B2 | 5/2015 | Scheller et al. | |
| 9,023,020 B2 | 5/2015 | Scheller et al. | |
| 9,039,686 B2 | 5/2015 | Scheller et al. | |
| 9,089,399 B2 | 7/2015 | Scheller et al. | |
| 9,107,682 B2 | 8/2015 | Scheller et al. | |
| 9,113,995 B2 | 8/2015 | Scheller et al. | |
| 9,119,702 B2 | 9/2015 | Scheller et al. | |
| 2003/0171762 A1 | 9/2003 | Forchette et al. | |
| 2004/0181138 A1 | 9/2004 | Hindricks et al. | |
| 2004/0249367 A1 | 12/2004 | Saadat et al. | |
| 2005/0054900 A1 | 3/2005 | Mawn et al. | |
| 2005/0154379 A1 | 7/2005 | McGowen, Sr. et al. | |
| 2005/0157985 A1 | 7/2005 | McGowan, Sr. et al. | |
| 2005/0234437 A1 | 10/2005 | Baxter et al. | |
| 2005/0272975 A1 | 12/2005 | McWeeny et al. | |
| 2005/0277874 A1 | 12/2005 | Selkee | |
| 2006/0129175 A1 | 6/2006 | Griffen et al. | |
| 2006/0178674 A1 | 8/2006 | McIntyre | |
| 2006/0293270 A1 | 12/2006 | Adamis et al. | |
| 2007/0185514 A1 | 8/2007 | Kirchhevel | |
| 2007/0260231 A1 | 11/2007 | Rose et al. | |
| 2008/0132761 A1 | 6/2008 | Sonnenschein et al. | |
| 2008/0287938 A1 | 11/2008 | Scheller et al. | |
| 2009/0018993 A1 | 1/2009 | Dick et al. | |
| 2009/0163943 A1 | 6/2009 | Cavanaugh et al. | |
| 2009/0187170 A1 | 7/2009 | Auld et al. | |
| 2009/0312750 A1* | 12/2009 | Spaide ................ A61F 9/008 606/4 |
| 2010/0004642 A1 | 1/2010 | Lumpkin | |
| 2010/0191224 A1 | 7/2010 | Butcher | |
| 2010/0268234 A1 | 10/2010 | Aho et al. | |
| 2010/0331883 A1 | 12/2010 | Schmitz et al. | |
| 2011/0028947 A1 | 2/2011 | Scheller et al. | |
| 2011/0144630 A1 | 6/2011 | Loeb | |
| 2012/0116361 A1 | 5/2012 | Hanlon et al. | |
| 2012/0245569 A1 | 9/2012 | Papac et al. | |
| 2013/0035551 A1 | 2/2013 | Yu et al. | |
| 2013/0060240 A1 | 3/2013 | Scheller et al. | |
| 2013/0071507 A1 | 3/2013 | Scheller et al. | |
| 2013/0090635 A1 | 4/2013 | Mansour | |
| 2013/0096541 A1 | 4/2013 | Scheller et al. | |
| 2013/0116671 A1 | 5/2013 | Scheller et al. | |
| 2013/0144278 A1 | 6/2013 | Papac et al. | |
| 2013/0150838 A1 | 6/2013 | Scheller et al. | |
| 2013/0165910 A1 | 6/2013 | Scheller et al. | |
| 2013/0261610 A1 | 10/2013 | LaConte et al. | |
| 2013/0281994 A1 | 10/2013 | Scheller et al. | |
| 2013/0304043 A1 | 11/2013 | Scheller et al. | |
| 2013/0304048 A1 | 11/2013 | Scheller et al. | |
| 2014/0005642 A1 | 1/2014 | Scheller et al. | |
| 2014/0039471 A1 | 2/2014 | Scheller et al. | |
| 2014/0039472 A1 | 2/2014 | Scheller et al. | |
| 2014/0039475 A1 | 2/2014 | Scheller et al. | |
| 2014/0046307 A1 | 2/2014 | Scheller et al. | |
| 2014/0052115 A1 | 2/2014 | Zeid et al. | |
| 2014/0066907 A1 | 3/2014 | Scheller et al. | |
| 2014/0066912 A1 | 3/2014 | Scheller et al. | |
| 2014/0074073 A1 | 3/2014 | Scheller et al. | |
| 2014/0074079 A1 | 3/2014 | Scheller et al. | |
| 2014/0088572 A1 | 3/2014 | Scheller et al. | |
| 2014/0088576 A1 | 3/2014 | Scheller et al. | |
| 2014/0107628 A1 | 4/2014 | Scheller et al. | |
| 2014/0107629 A1 | 4/2014 | Scheller et al. | |
| 2015/0038950 A1 | 2/2015 | Scheller et al. | |

OTHER PUBLICATIONS

Ferry P.W. Melchels, Jan Feijen, Dirk W. Grijpma, A review on stereolithography and its applications in biomedical engineering, Biomaterials 31 (2010) 6121-6130.

* cited by examiner

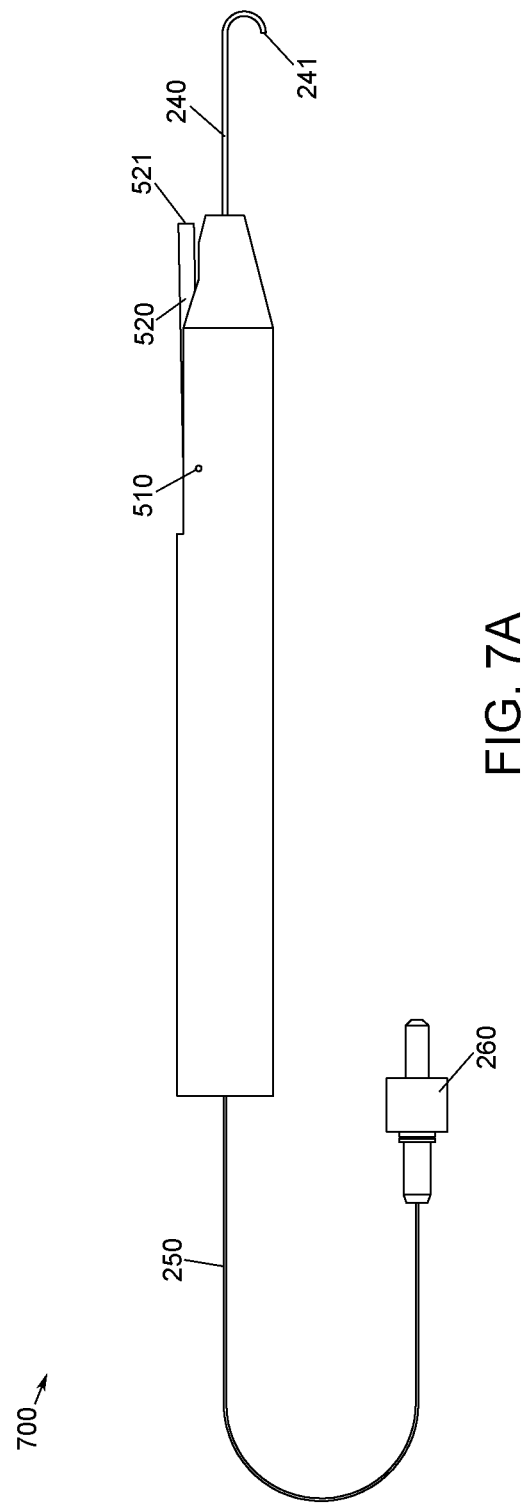

STEERABLE LASER PROBE

CROSS-REFERENCE TO RELATED APPLICATIONS

This non-provisional application is a divisional application of U.S. Ser. No. 15/377,586, filed Dec. 13, 2016, which derives and claims priority from U.S. Pat. No. 9,549,780, filed on Apr. 14, 2013, which derives and claims priority from provisional application 61/646,366, filed on May 13, 2012.

FIELD OF THE INVENTION

The present disclosure relates to a surgical instrument, and, more particularly, to a steerable laser probe.

BACKGROUND OF THE INVENTION

A wide variety of ophthalmic procedures require a laser energy source. For example, ophthalmic surgeons may use laser photocoagulation to treat proliferative retinopathy. Proliferative retinopathy is a condition characterized by the development of abnormal blood vessels in the retina that grow into the vitreous humor. Ophthalmic surgeons may treat this condition by energizing a laser to cauterize portions of the retina to prevent the ab-normal blood vessels from growing and hemorrhaging.

In order to increase the chances of a successful laser photocoagulation procedure, it is important that a surgeon is able aim the laser at a plurality of targets within the eye, e.g., by guiding or moving the laser from a first target to a second target within the eye. It is also important that the surgeon is able to easily control a movement of the laser. For example, the surgeon must be able to easily direct a laser beam by steering the beam to a first position aimed at a first target, guide the laser beam from the first position to a second position aimed at a second target, and hold the laser beam in the second position. Accordingly, there is a need for a surgical laser probe that can be easily guided to a plurality of targets within the eye.

BRIEF SUMMARY OF THE INVENTION

The present disclosure presents a steerable laser probe. In one or more embodiments, a steerable laser probe may comprise a handle having a handle distal end and a handle proximal end, an actuation lever of the handle, a flexible housing tube having a flexible housing tube distal end and a flexible housing tube proximal end, and an optic fiber disposed within an inner bore of the handle and the flexible housing tube. Illustratively, an actuation of the actuation lever may be configured to gradually curve the flexible housing tube. In one or more embodiments, a gradual curving of the flexible housing tube may be configured to gradually curve the optic fiber. Illustratively, an actuation of the actuation lever may be configured to gradually straighten the flexible housing tube. In one or more embodiments, a gradual straightening of the flexible housing tube may be configured to gradually straighten the optic fiber.

BRIEF DESCRIPTION OF THE DRAWINGS

The above and further advantages of the present invention may be better understood by referring to the following description in conjunction with the accompanying drawings in which like reference numerals indicate identical or functionally similar elements:

FIGS. 7A, 7B, 7C, 7D, and 7E illustrate a gradual straightening of an optic fiber.

DETAILED DESCRIPTION OF AN ILLUSTRATIVE EMBODIMENT

Figure 1A:
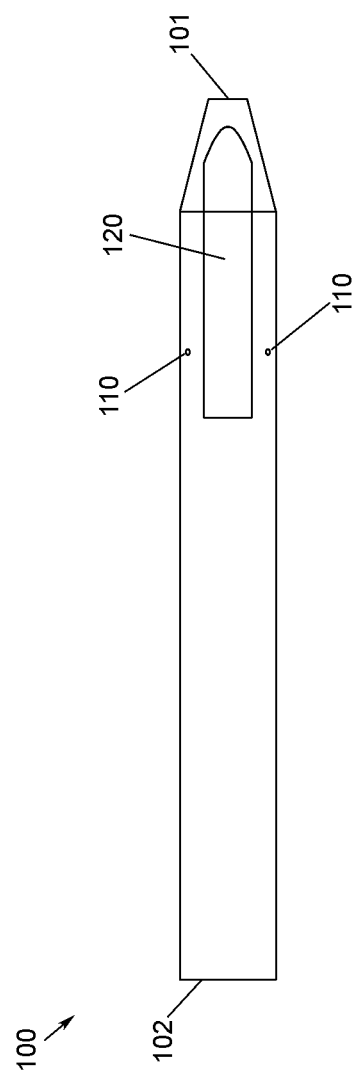
FIGS. 1A and 1B are schematic diagrams illustrating a handle.
Figure 1B:
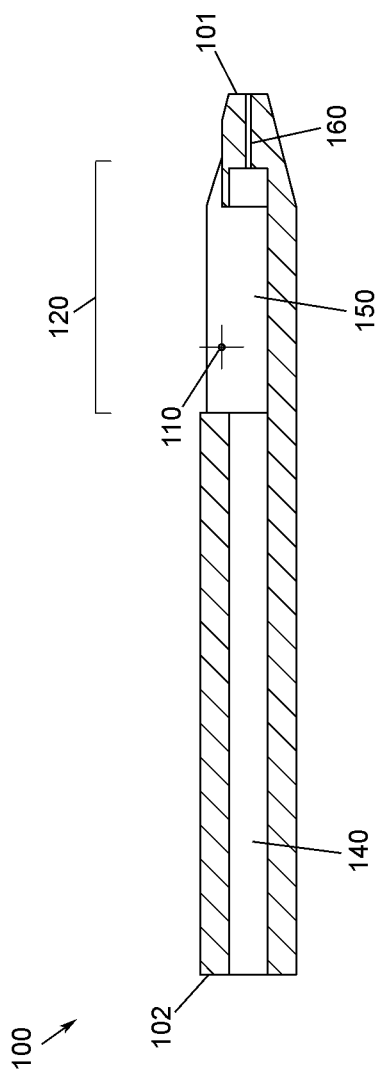

FIGS. 1A and 1B are schematic diagrams illustrating a handle 100. FIG. 1A illustrates a top view of handle 100. In one or more embodiments, handle 100 may comprise a handle distal end 101, a handle proximal end 102, a pivot pin housing 110, and an actuation lever channel 120. FIG. 1B illustrates a cross-sectional view of handle 100. In one or more embodiments, handle 100 may comprise an inner bore 140, an actuation lever guide 150, and an optic fiber guide 160. Handle 100 may be manufactured from any suitable material, e.g., polymers, metals, metal alloys, etc., or from any combination of suitable materials.

Figure 2:
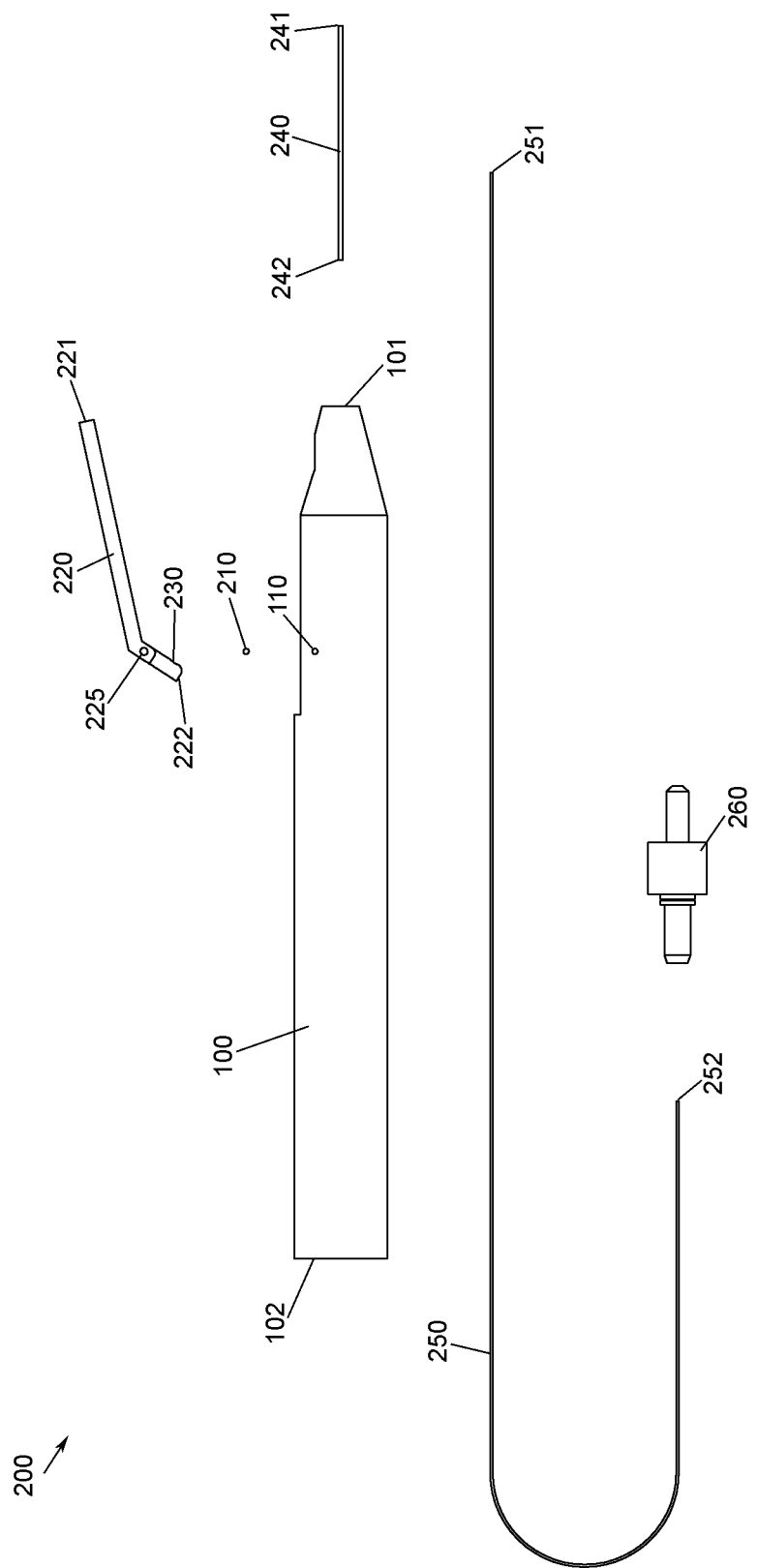
FIG. 2 is a schematic diagram illustrating an exploded view of a steerable laser probe assembly.

FIG. 2 is a schematic diagram illustrating an exploded view of a steerable laser probe assembly 200. In one or more embodiments, steerable laser probe assembly 200 may comprise a handle 100, a pivot pin 210, an actuation lever 220 having an actuation lever distal end 221 and an actuation lever proximal end 222, a flexible housing tube 240 having a flexible housing tube distal end 241 and a flexible housing tube proximal end 242, an optic fiber 250 having an optic fiber distal end 251 and an optic fiber proximal end 252, and a light source interface 260. Illustratively, light source interface 260 may be configured to interface with optic fiber 250, e.g., at optic fiber proximal end 252. In one or more embodiments, light source interface 260 may comprise a standard light source connecter, e.g., an SMA connector.

Illustratively, a portion of flexible housing tube 240 may be fixed to handle distal end 101, e.g., flexible housing tube proximal end 242 may be fixed to handle distal end 101. In one or more embodiments, a portion of flexible housing tube 240 may be fixed to handle distal end 101, e.g., by an adhesive or any suitable fixation means. Illustratively, a portion of flexible housing tube 240 may be disposed within optic fiber guide 160, e.g., flexible housing tube proximal end 242 may be disposed within optic fiber guide 160. In one or more embodiments, a portion of flexible housing tube 240 may be fixed within optic fiber guide 160, e.g., by an adhesive or any suitable fixation means. Flexible housing tube 240 may be manufactured from any suitable material, e.g., polymers, metals, metal alloys, etc., or from any combination of suitable materials. Illustratively, flexible housing tube 240 may comprise a shape memory material, e.g., Nitinol. In one or more embodiments, flexible housing tube 240 may be manufactured from a material having an ultimate tensile strength between 700 and 1000 MPa. Illustratively, flexible housing tube 240 may be manufactured from a material having ultimate tensile strength less than 700 MPa or greater than 1000 MPa. In one or more embodiments, flexible housing tube 240 may be manufactured from a material having a modulus of elasticity between 30 and 80 GPa. Illustratively, flexible housing tube 240 may be manufactured from a material having a modulus of elasticity less than 30 GPa or greater than 80 GPa. In one or more embodiments, flexible housing tube 240 may be manufactured with dimensions suitable for performing microsurgical procedures, e.g., ophthalmic surgical procedures. Illustratively, flexible housing tube 240 may have an ultimate tensile strength between 1000 MPa and 1100 MPa. In one or more embodiments, flexible housing tube 240 may have an ultimate tensile strength less than 1000 MPa or greater than 1100 MPa.

Illustratively, a portion of actuation lever 220 may be disposed within actuation lever guide 150, e.g., actuation lever proximal end 222 may be disposed within actuation lever guide 150. In one or more embodiments, actuation lever 220 may comprise a pivot pin chamber 225 configured to enclose a portion of pivot pin 210. Illustratively, pivot pin 210 may be disposed within both pivot pin housing 110 and pivot pin chamber 225. In one or more embodiments, pivot pin 210 may be fixed within pivot pin housing 110. Illustratively, pivot pin 210 may be fixed within pivot pin housing 110, e.g., by an adhesive or any suitable fixation means. In one or more embodiments, pivot pin 210 may be configured to fix a portion of actuation lever 220 to handle 100, e.g., at pivot pin chamber 225. Illustratively, when pivot pin 210 is disposed within pivot pin chamber 225, pivot pin 210 may be configured to limit an actuation of actuation lever 220, e.g., to allow rotational actuation of actuation lever 220 about pivot pin 210. In one or more embodiments, actuation lever 220 may be configured to rotate about pivot pin 210, e.g., in response to an application of a force to a portion of actuation lever 220. Illustratively, pivot pin chamber 225 may be coated with a material, e.g., Teflon, configured to facilitate a rotation of actuation lever 220 about pivot pin 210.

Illustratively, actuation lever 220 may comprise an optic fiber housing 230 configured to house a portion of optic fiber 250. In one or more embodiments, optic fiber 250 may be disposed within inner bore 140, actuation lever guide 150, optic fiber housing 230, optic fiber guide 160, and flexible housing tube 240. Illustratively, optic fiber 250 may be disposed within flexible housing tube 240 wherein optic fiber distal end 251 may be adjacent to flexible housing tube distal end 241. In one or more embodiments, a portion of optic fiber 250 may be fixed to an inner portion of flexible housing tube 240. Illustratively, a portion of optic fiber 250 may be fixed within flexible housing tube 240, e.g., by an adhesive or any suitable fixation means. In one or more embodiments, a portion of optic fiber 250 may be fixed within optic fiber housing 230, e.g., by an adhesive or any suitable fixation means. Illustratively, optic fiber 250 may be fixed within flexible housing tube 240 and optic fiber housing 230.

In one or more embodiments, a surgeon may actuate actuation lever 220, e.g., by applying a force to a portion of actuation lever 220. Illustratively, an application of a force to actuation lever 220 may be configured to actuate actuation lever distal end 221 about pivot pin 210, e.g., in a clockwise direction. In one or more embodiments, an actuation of actuation lever distal end 221 about pivot pin 210 in a clockwise direction may be configured to actuate actuation lever proximal end 222 about pivot pin 210, e.g., in a clockwise direction. Illustratively, an actuation of actuation lever proximal end 222 about pivot pin 210 in a clockwise direction may be configured to actuate optic fiber housing 230 within actuation lever guide 150, e.g., towards handle proximal end 102 and away from handle distal end 101. In one or more embodiments, an actuation of optic fiber housing 230 towards handle proximal end 102 and away from handle distal end 101 may be configured to retract optic fiber 250 relative to flexible housing tube 240. Illustratively, a retraction of optic fiber 250 relative to flexible housing tube 240 may be configured to apply a force, e.g., a compressive force, to a portion of flexible housing tube 240. In one or more embodiments, an application of a force to a portion of flexible housing tube 240 may be configured to compress a portion of flexible housing tube 240. Illustratively, a compression of a portion of flexible housing tube 240 may be configured to cause flexible housing tube 240 to gradually curve. In one or more embodiments, a gradual curving of flexible housing tube 240 may be configured to gradually curve optic fiber 250. Illustratively, an actuation of actuation lever distal end 221 about pivot pin 210 in a clockwise direction may be configured to gradually curve optic fiber 250, e.g. an application of a force to a portion of actuation lever 220 may be configured to gradually curve optic fiber 250.

In one or more embodiments, a surgeon may actuate actuation lever 220, e.g., by reducing a force applied to a portion of actuation lever 220. Illustratively, a reduction of a force applied to actuation lever 220 may be configured to actuate actuation lever distal end 221 about pivot pin 210, e.g., in a counter-clockwise direction. In one or more embodiments, an actuation of actuation lever distal end 221 about pivot pin 210 in a counter-clockwise direction may be configured to actuate actuation lever proximal end 222 about pivot pin 210, e.g., in a counter-clockwise direction. Illustratively, an actuation of actuation lever proximal end 222 about pivot pin 210 in a counter-clockwise direction may be configured to actuate optic fiber housing 230 within actuation lever guide 150, e.g., towards handle distal end 101 and away from handle proximal end 102. In one or more embodiments, an actuation of optic fiber housing 230 towards handle distal end 101 and away from handle proximal end 102 may be configured to extend optic fiber 250 relative to flexible housing tube 240. Illustratively, an extension of optic fiber 250 relative to flexible housing tube 240 may be configured to reduce a force, e.g., a compressive force, applied to a portion of flexible housing tube 240. In one or more embodiments, a reduction of a force applied to a portion of flexible housing tube 240 may be configured to decompress a portion of flexible housing tube 240. Illustratively, a decompression of a portion of flexible housing tube 240 may be configured to cause flexible housing tube 240 to gradually straighten. In one or more embodiments, a gradual straightening of flexible housing tube 240 may be configured to gradually straighten optic fiber 250. Illustratively, an actuation of actuation lever distal end 221 about pivot pin 210 in a counter-clockwise direction may be configured to gradually straighten optic fiber 250, e.g., a reduction of a force applied to portion of actuation lever 220 may be configured to gradually curve optic fiber 250.

Figure 3A:
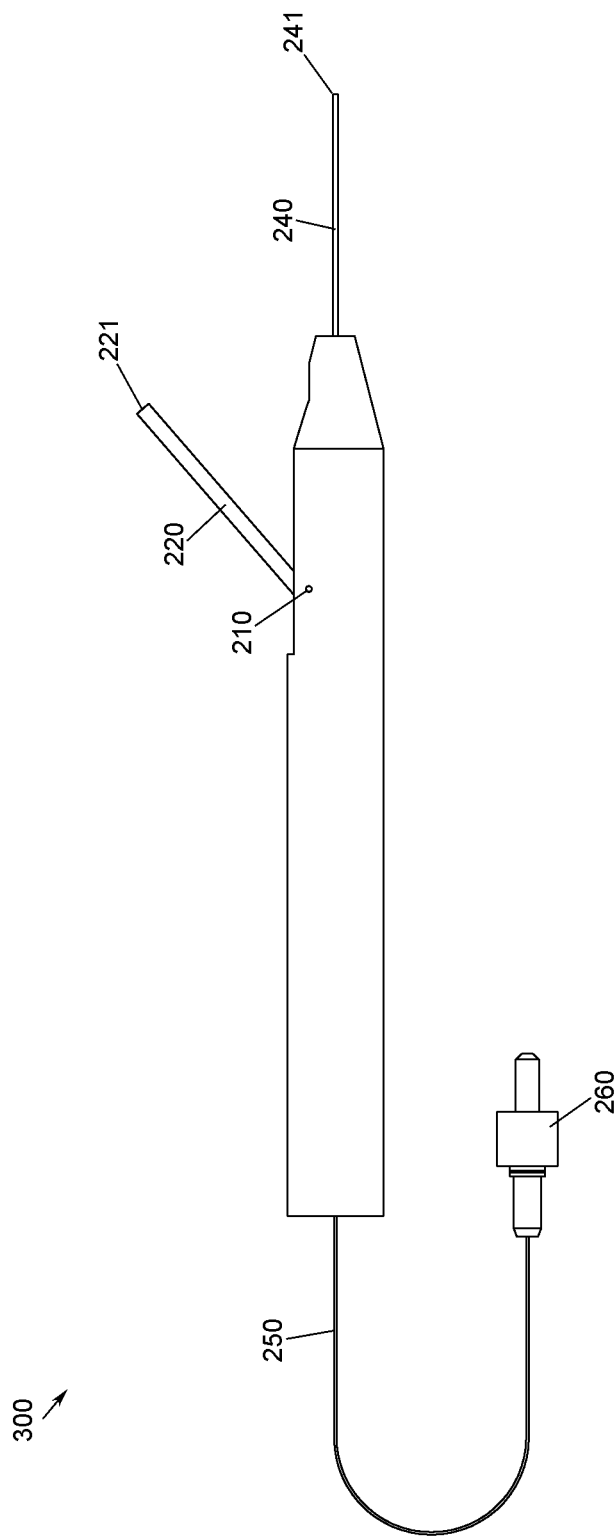
FIGS. 3A, 3B, 3C, 3D, and 3E illustrate a gradual curving of an optic fiber.

FIGS. 3A, 3B, 3C, 3D, and 3E illustrate a gradual curving of an optic fiber 250. FIG. 3A illustrates a straight optic fiber 300. In one or more embodiments, optic fiber 250 may comprise a straight optic fiber 300, e.g., when optic fiber 250 is fully extended relative to flexible housing tube 240. For example, optic fiber 250 may comprise a straight optic fiber 300 when optic fiber housing 230 is fully extended relative to flexible housing tube 240. Illustratively, optic fiber 250 may comprise a straight optic fiber 300, e.g., when a portion of flexible housing tube 240 is fully decompressed. In one or more embodiments, optic fiber 250 may comprise a straight optic fiber 300, e.g., when no force is applied to actuation lever 220. Illustratively, a line tangent to optic fiber distal end 251 may be parallel to a line tangent to flexible housing tube proximal end 242, e.g., when optic fiber 250 comprises a straight optic fiber 300.

Figure 3B:
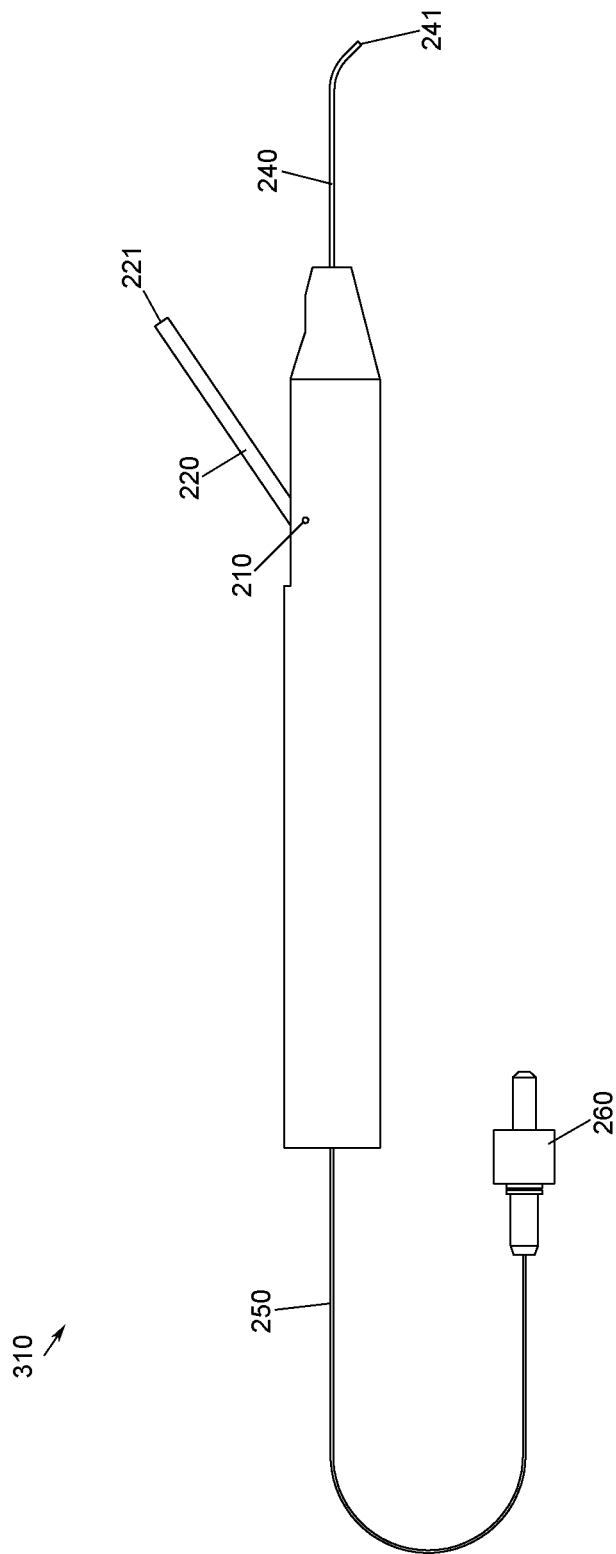

FIG. 3B illustrates an optic fiber in a first curved position 310. In one or more embodiments, a rotation of actuation lever 220 about pivot pin 210 in a clockwise direction may be configured to gradually curve optic fiber 250 from a straight optic fiber 300 to an optic fiber in a first curved position 310. Illustratively, an application of a force to a portion of actuation lever 220 may be configured to rotate actuation lever distal end 221 about pivot pin 210 in a clockwise direction. In one or more embodiments, a rotation of actuation lever distal end 221 about pivot pin 210 in a clockwise direction may be configured to actuate optic fiber housing 230, e.g., towards handle proximal end 102 and away from handle distal end 101. Illustratively, an actuation of optic fiber housing 230 towards handle proximal end 102 and away from handle distal end 101 may be configured to retract optic fiber 250 relative to flexible housing tube 240. In one or more embodiments, a retraction of optic fiber 250 relative to flexible housing tube 240 may be configured to apply a compressive force to a portion of flexible housing tube 240. Illustratively, an application of a compressive force to a portion of flexible housing tube 240 may be configured to compress a portion of flexible housing tube 240 causing flexible housing tube 240 to gradually curve. In one or more embodiments, a gradual curving of flexible housing tube 240 may be configured to gradually curve optic fiber 250, e.g., from a straight optic fiber 300 to an optic fiber in a first curved position 310. Illustratively, a line tangent to optic fiber distal end 251 may intersect a line tangent to flexible housing tube proximal end 242 at a first angle, e.g., when optic fiber 250 comprises an optic fiber in a first curved position 310. In one or more embodiments, the first angle may comprise any angle greater than zero degrees. For example, the first angle may comprise a 45 degree angle.

Figure 3C:
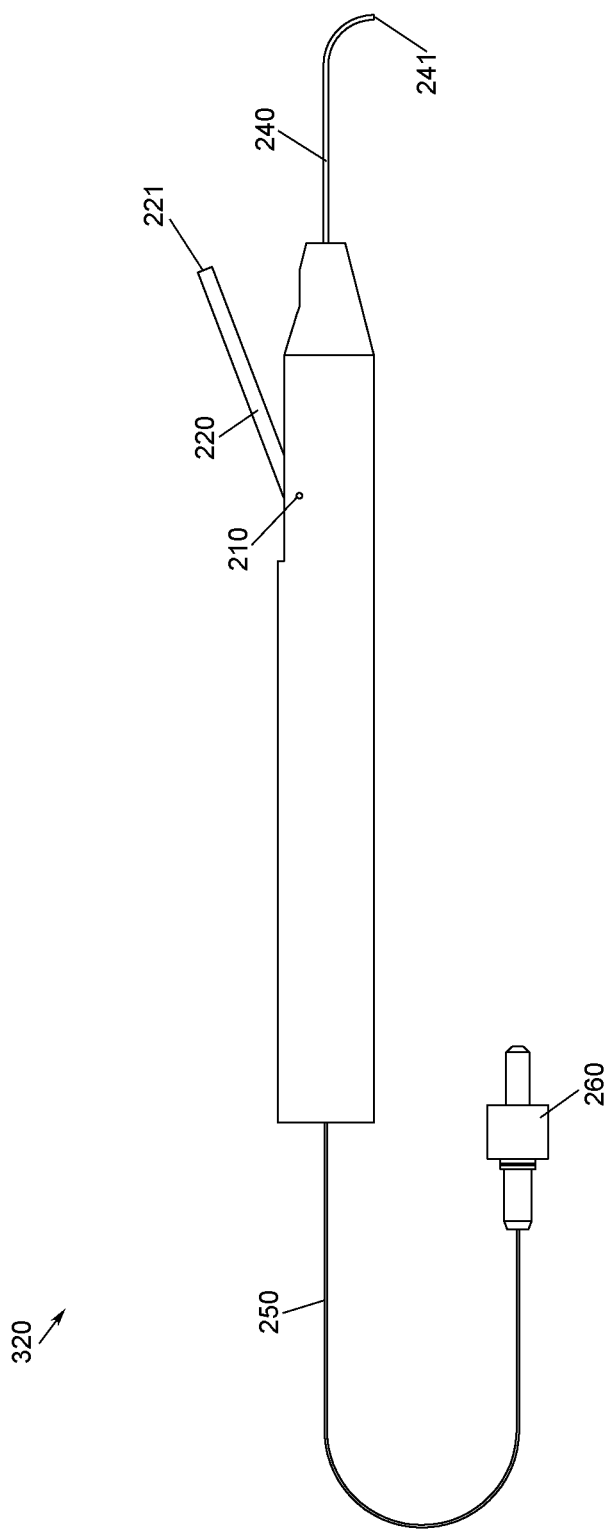

FIG. 3C illustrates an optic fiber in a second curved position 320. In one or more embodiments, a rotation of actuation lever 220 about pivot pin 210 in a clockwise direction may be configured to gradually curve optic fiber 250 from an optic fiber in a first curved position 310 to an optic fiber in a second curved position 320. Illustratively, an application of a force to a portion of actuation lever 220 may be configured to rotate actuation lever distal end 221 about pivot pin 210 in a clockwise direction. In one or more embodiments, a rotation of actuation lever distal end 221 about pivot pin 210 in a clockwise direction may be configured to actuate optic fiber housing 230, e.g., towards handle proximal end 102 and away from handle distal end 101. Illustratively, an actuation of optic fiber housing 230 towards handle proximal end 102 and away from handle distal end 101 may be configured to retract optic fiber 250 relative to flexible housing tube 240. In one or more embodiments, a retraction of optic fiber 250 relative to flexible housing tube 240 may be configured to apply a compressive force to a portion of flexible housing tube 240. Illustratively, an application of a compressive force to a portion of flexible housing tube 240 may be configured to compress a portion of flexible housing tube 240 causing flexible housing tube 240 to gradually curve. In one or more embodiments, a gradual curving of flexible housing tube 240 may be configured to gradually curve optic fiber 250, e.g., from an optic fiber in a first curved position 310 to an optic fiber in a second curved position 320. Illustratively, a line tangent to optic fiber distal end 251 may intersect a line tangent to flexible housing tube proximal end 242 at a second angle, e.g., when optic fiber 250 comprises an optic fiber in a second curved position 320. In one or more embodiments, the second angle may comprise any angle greater than the first angle. For example, the second angle may comprise a 90 degree angle.

Figure 3D:
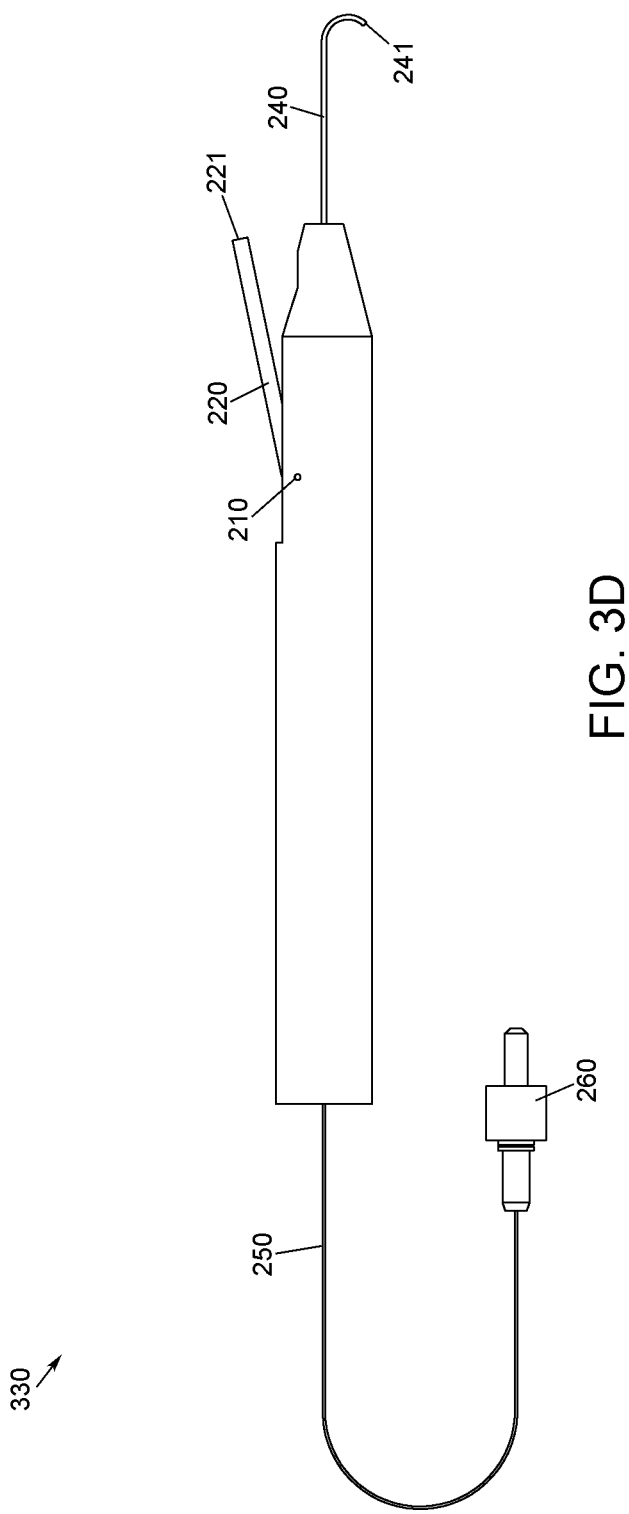

FIG. 3D illustrates an optic fiber in a third curved position 330. In one or more embodiments, a rotation of actuation lever 220 about pivot pin 210 in a clockwise direction may be configured to gradually curve optic fiber 250 from an optic fiber in a second curved position 320 to an optic fiber in a third curved position 330. Illustratively, an application of a force to a portion of actuation lever 220 may be configured to rotate actuation lever distal end 221 about pivot pin 210 in a clockwise direction. In one or more embodiments, a rotation of actuation lever distal end 221 about pivot pin 210 in a clockwise direction may be configured to actuate optic fiber housing 230, e.g., towards handle proximal end 102 and away from handle distal end 101. Illustratively, an actuation of optic fiber housing 230 towards handle proximal end 102 and away from handle distal end 101 may be configured to retract optic fiber 250 relative to flexible housing tube 240. In one or more embodiments, a retraction of optic fiber 250 relative to flexible housing tube 240 may be configured to apply a compressive force to a portion of flexible housing tube 240. Illustratively, an application of a compressive force to a portion of flexible housing tube 240 may be configured to compress a portion of flexible housing tube 240 causing flexible housing tube 240 to gradually curve. In one or more embodiments, a gradual curving of flexible housing tube 240 may be configured to gradually curve optic fiber 250, e.g., from an optic fiber in a second curved position 320 to an optic fiber in a third curved position 330. Illustratively, a line tangent to optic fiber distal end 251 may intersect a line tangent to flexible housing tube proximal end 242 at a third angle, e.g., when optic fiber 250 comprises an optic fiber in a third curved position 330. In one or more embodiments, the third angle may comprise any angle greater than the second angle. For example, the third angle may comprise a 135 degree angle.

Figure 3E:
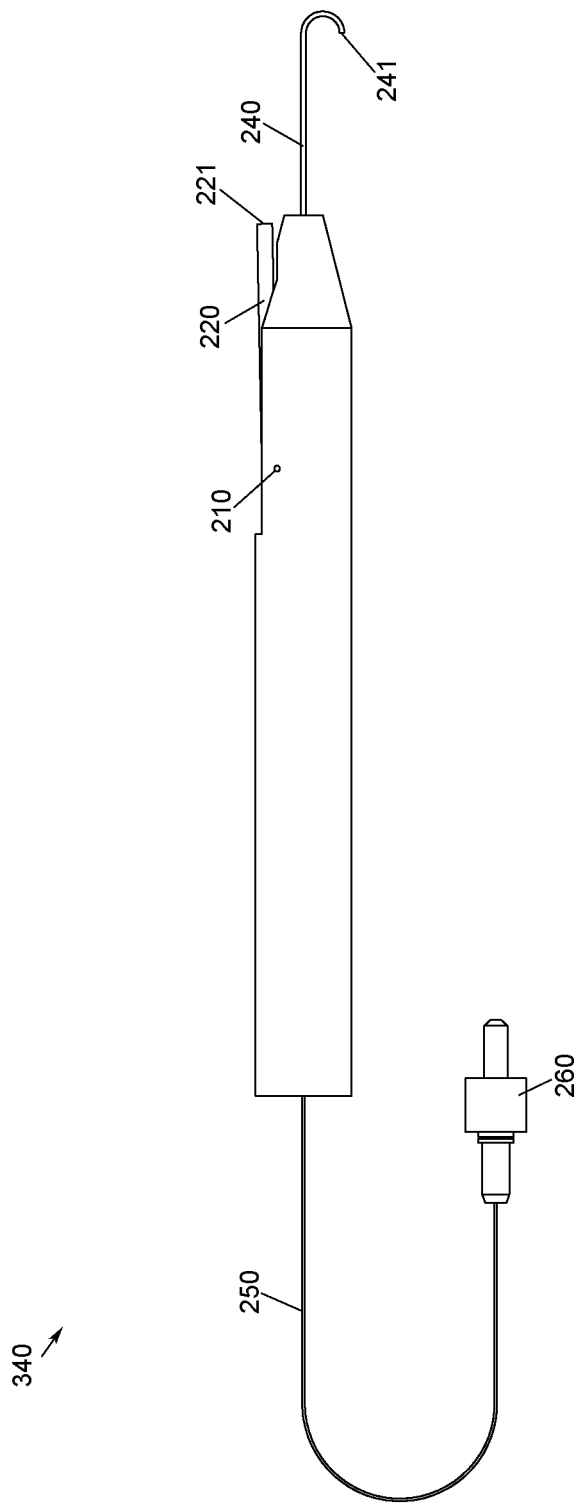

FIG. 3E illustrates an optic fiber in a fourth curved position 340. In one or more embodiments, a rotation of actuation lever 220 about pivot pin 210 in a clockwise direction may be configured to gradually curve optic fiber 250 from an optic fiber in a third curved position 330 to an optic fiber in a fourth curved position 340. Illustratively, an application of a force to a portion of actuation lever 220 may be configured to rotate actuation lever distal end 221 about pivot pin 210 in a clockwise direction. In one or more embodiments, a rotation of actuation lever distal end 221 about pivot pin 210 in a clockwise direction may be configured to actuate optic fiber housing 230, e.g., towards handle proximal end 102 and away from handle distal end 101. Illustratively, an actuation of optic fiber housing 230 towards handle proximal end 102 and away from handle distal end 101 may be configured to retract optic fiber 250 relative to flexible housing tube 240. In one or more embodiments, a retraction of optic fiber 250 relative to flexible housing tube 240 may be configured to apply a compressive force to a portion of flexible housing tube 240. Illustratively, an application of a compressive force to a portion of flexible housing tube 240 may be configured to compress a portion of flexible housing tube 240 causing flexible housing tube 240 to gradually curve. In one or more embodiments, a gradual curving of flexible housing tube 240 may be configured to gradually curve optic fiber 250, e.g., from an optic fiber in a third curved position 330 to an optic fiber in a fourth curved position 340. Illustratively, a line tangent to optic fiber distal end 251 may be parallel to a line tangent to flexible housing tube proximal end 242, e.g., when optic fiber 250 comprises an optic fiber in a fourth curved position 340.

In one or more embodiments, one or more properties of a steerable laser probe may be adjusted to attain one or more desired steerable laser probe features. For example, a length that flexible housing tube distal end 241 extends from handle distal end 101 may be adjusted to vary a degree of rotation of actuation lever 220 configured to curve flexible housing tube 240 to a particular curved position. In one or more embodiments, a stiffness of flexible housing tube 240 may be adjusted to vary a degree of rotation of actuation lever 220 configured to curve flexible housing tube 240 to a particular curved position. Illustratively, a material comprising flexible housing tube 240 may be adjusted to vary a degree of rotation of actuation lever 220 configured to curve flexible housing tube 240 to a particular curved position.

Illustratively, a position of pivot pin 210 may be adjusted to vary a degree of rotation of actuation lever 220 configured to curve flexible housing tube 240 to a particular curved position. In one or more embodiments, a geometry of actuation lever 220 may be adjusted to vary a degree of rotation of actuation lever 220 configured to curve flexible housing tube 240 to a particular curved position. Illustratively, one or more locations within flexible housing tube 240 wherein optic fiber 250 may be fixed to an inner portion of flexible housing tube 240 may be adjusted to vary a degree of rotation of actuation lever 220 configured to curve flexible housing tube 240 to a particular curved position.

In one or more embodiments, a mechanism configured to control a gradual curving of optic fiber 250 or a gradual straightening of optic fiber 250 may be varied to, e.g., attain one or more desired steerable laser probe features. Illustratively, a mechanism configured to control a gradual curving of optic fiber 250 may or may not be configured to control a gradual straightening of optic fiber 250. In one or more embodiments, a mechanism configured to control a gradual straightening of optic fiber 250 may or may not be configured to control a gradual curving of optic fiber 250. Illustratively, a steerable laser probe may be modified to allow a surgeon to selectively fix optic fiber 250 in a particular curved position. In one or more embodiments, a detent or a pawl may be added to a steerable laser probe, e.g., to temporarily fix actuation lever 220 in a position relative to handle proximal end 102. Illustratively, one or more magnets may be added to a steerable laser probe, e.g., to temporarily fix actuation lever 220 in a position relative to handle proximal end 102. In one or more embodiments, a switch or any other suitable control mechanism may be added to a steerable laser probe to control a gradual curving of optic fiber 250 or a gradual straightening of optic fiber 250.

In one or more embodiments, at least a portion of optic fiber 250 may be enclosed in an optic fiber sleeve configured to, e.g., protect optic fiber 250, vary a stiffness of optic fiber 250, vary an optical property of optic fiber 250, etc. Illustratively, an optic fiber sleeve may be configured to compress a portion of flexible housing tube 240. For example, an optic fiber sleeve may enclose a portion of optic fiber 250 and the optic fiber sleeve may be fixed within optic fiber housing 230 and also fixed to a portion of flexible housing tube 240. In one or more embodiments, a rotation of actuation lever 220 about pivot pin 210 in a clockwise direction may be configured to retract an optic fiber sleeve relative to flexible housing tube 240. Illustratively, a retraction of an optic fiber sleeve relative to flexible housing tube 240 may be configured to cause the optic fiber sleeve to apply a force, e.g., a compressive force, to a portion of flexible housing tube 240. In one or more embodiments, an application of a force to a portion of flexible housing tube 240 may be configured to compress a portion of flexible housing tube 240 causing flexible housing tube 240 to gradually curve.

Figure 4A:
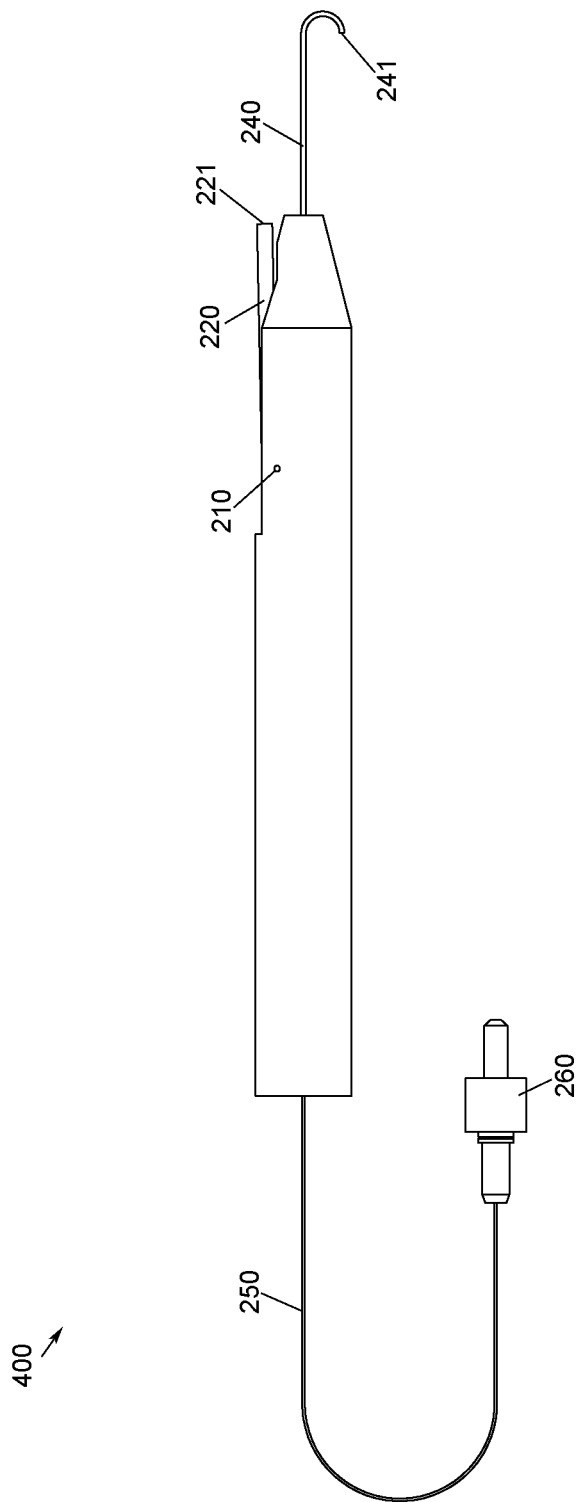
FIGS. 4A, 4B, 4C, 4D, and 4E illustrate a gradual straightening of an optic fiber.

FIGS. 4A, 4B, 4C, 4D, and 4E illustrate a gradual straightening of an optic fiber 250. FIG. 4A illustrates a fully curved optic fiber 400. In one or more embodiments, optic fiber 250 may comprise a fully curved optic fiber 400, e.g., when optic fiber 250 is fully retracted relative to flexible housing tube 240. For example, optic fiber 250 may comprise a fully curved optic fiber 400 when optic fiber housing 230 is fully retracted relative to flexible housing tube 240. Illustratively, optic fiber 250 may comprise a fully curved optic fiber 400, e.g., when a portion of flexible housing tube 240 is compressed. In one or more embodiments, optic fiber 250 may comprise a fully curved optic fiber 400, e.g., when a force is applied to actuation lever 220. Illustratively, a line tangent to optic fiber distal end 251 may be parallel to a line tangent to flexible housing tube proximal end 242, e.g., when optic fiber 250 comprises a fully curved optic fiber 400.

Figure 4B:
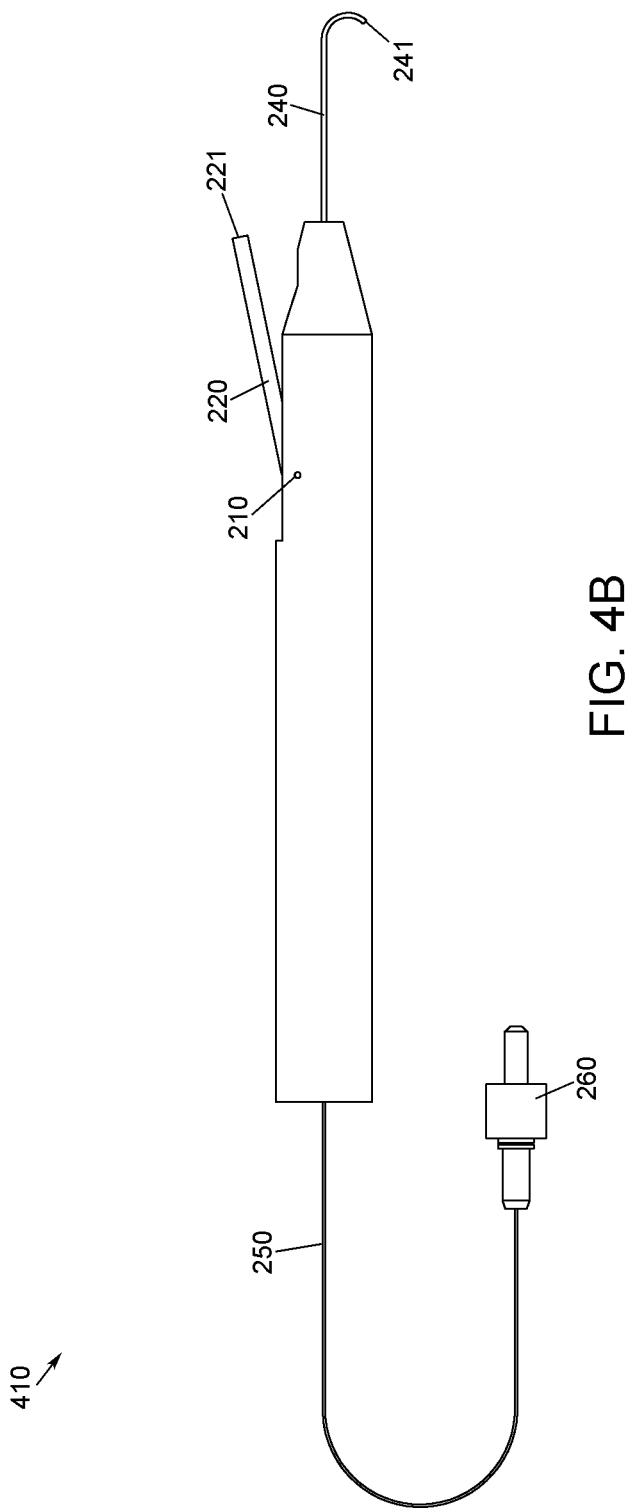

FIG. 4B illustrates an optic fiber in a first partially straightened position 410. In one or more embodiments, a rotation of actuation lever 220 about pivot pin 210 in a counter-clockwise direction may be configured to gradually straighten optic fiber 250 from a fully curved optic fiber 400 to an optic fiber in a first partially straightened position 410. Illustratively, a reduction of a force applied to a portion of actuation lever 220 may be configured to rotate actuation lever distal end 221 about pivot pin 210 in a counter-clockwise direction. In one or more embodiments, a rotation of actuation lever distal end 221 about pivot pin 210 in a counter-clockwise direction may be configured to actuate optic fiber housing 230, e.g., towards handle distal end 101 and away from handle proximal end 102. Illustratively, an actuation of optic fiber housing 230 towards handle distal end 101 and away from handle proximal end 102 may be configured to extend optic fiber 250 relative to flexible housing tube 240. In one or more embodiments, an extension of optic fiber 250 relative to flexible housing tube 240 may be configured to reduce a compressive force applied to a portion of flexible housing tube 240. Illustratively, a reduction of a compressive force applied to a portion of flexible housing tube 240 may be configured to decompress a portion of flexible housing tube 240 causing flexible housing tube 240 to gradually straighten. In one or more embodiments, a gradual straightening of flexible housing tube 240 may be configured to gradually straighten optic fiber 250, e.g., from a fully curved optic fiber 400 to an optic fiber in a first partially straightened position 410. Illustratively, a line tangent to optic fiber distal end 251 may intersect a line tangent to flexible housing tube proximal end 242 at a first partially straightened angle, e.g., when optic fiber 250 comprises an optic fiber in a first partially straightened position 410. In one or more embodiments, the first partially straightened angle may comprise any angle less than 180 degrees. For example, the first partially straightened angle may comprise a 135 degree angle.

Figure 4C:
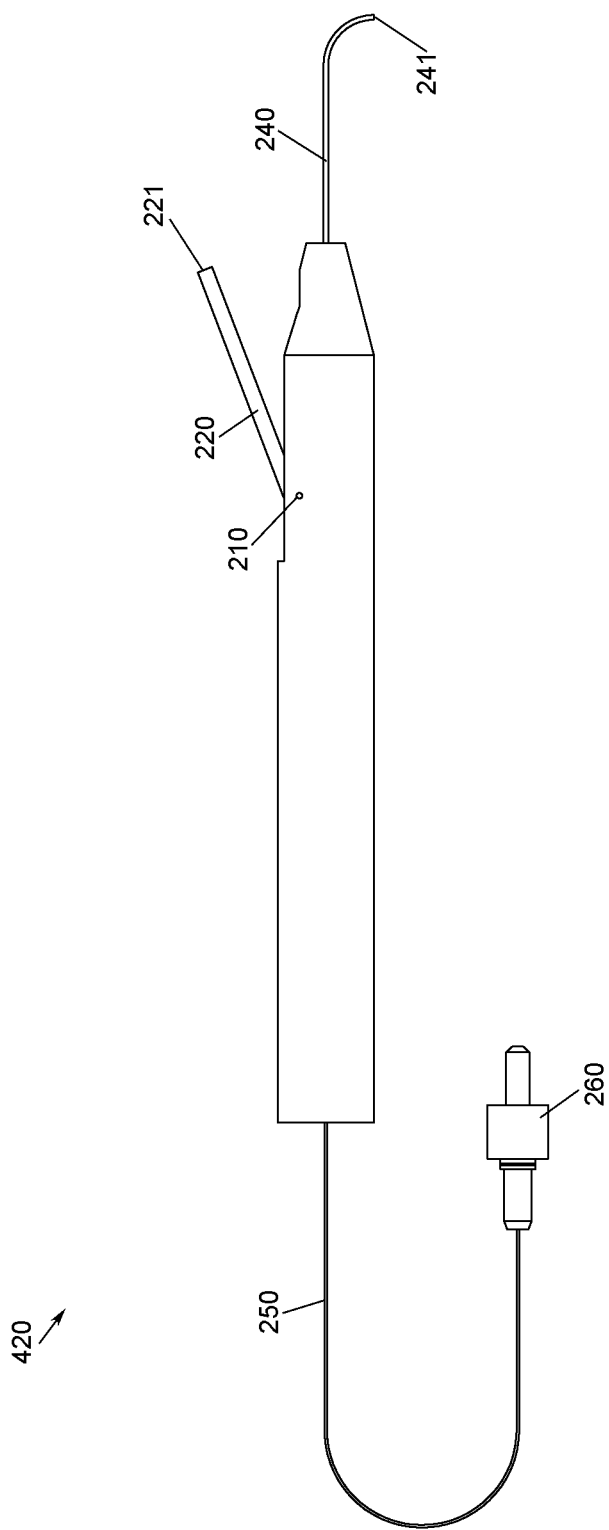

FIG. 4C illustrates an optic fiber in a second partially straightened position 420. In one or more embodiments, a rotation of actuation lever 220 about pivot pin 210 in a counter-clockwise direction may be configured to gradually straighten optic fiber 250 from an optic fiber in a first partially straightened position 410 to an optic fiber in a second partially straightened position 420. Illustratively, a reduction of a force applied to a portion of actuation lever 220 may be configured to rotate actuation lever distal end 221 about pivot pin 210 in a counter-clockwise direction. In one or more embodiments, a rotation of actuation lever distal end 221 about pivot pin 210 in a counter-clockwise direction may be configured to actuate optic fiber housing 230, e.g., towards handle distal end 101 and away from handle proximal end 102. Illustratively, an actuation of optic fiber housing 230 towards handle distal end 101 and away from handle proximal end 102 may be configured to extend optic fiber 250 relative to flexible housing tube 240. In one or more embodiments, an extension of optic fiber 250 relative to flexible housing tube 240 may be configured to reduce a compressive force applied to a portion of flexible housing tube 240. Illustratively, a reduction of a compressive force applied to a portion of flexible housing tube 240 may be configured to decompress a portion of flexible housing tube 240 causing flexible housing tube 240 to gradually straighten. In one or more embodiments, a gradual straightening of flexible housing tube 240 may be configured to gradually straighten optic fiber 250, e.g., from an optic fiber in a first partially straightened position 410 to an optic fiber in a second partially straightened position 420. Illustratively, a line tangent to optic fiber distal end 251 may intersect a line tangent to flexible housing tube proximal end 242 at a second partially straightened angle, e.g., when optic fiber 250 comprises an optic fiber in a second partially straightened position 420. In one or more embodiments, the second partially straightened angle may comprise any angle less than the first partially straightened angle. For example, the second partially straightened angle may comprise a 90 degree angle.

Figure 4D:
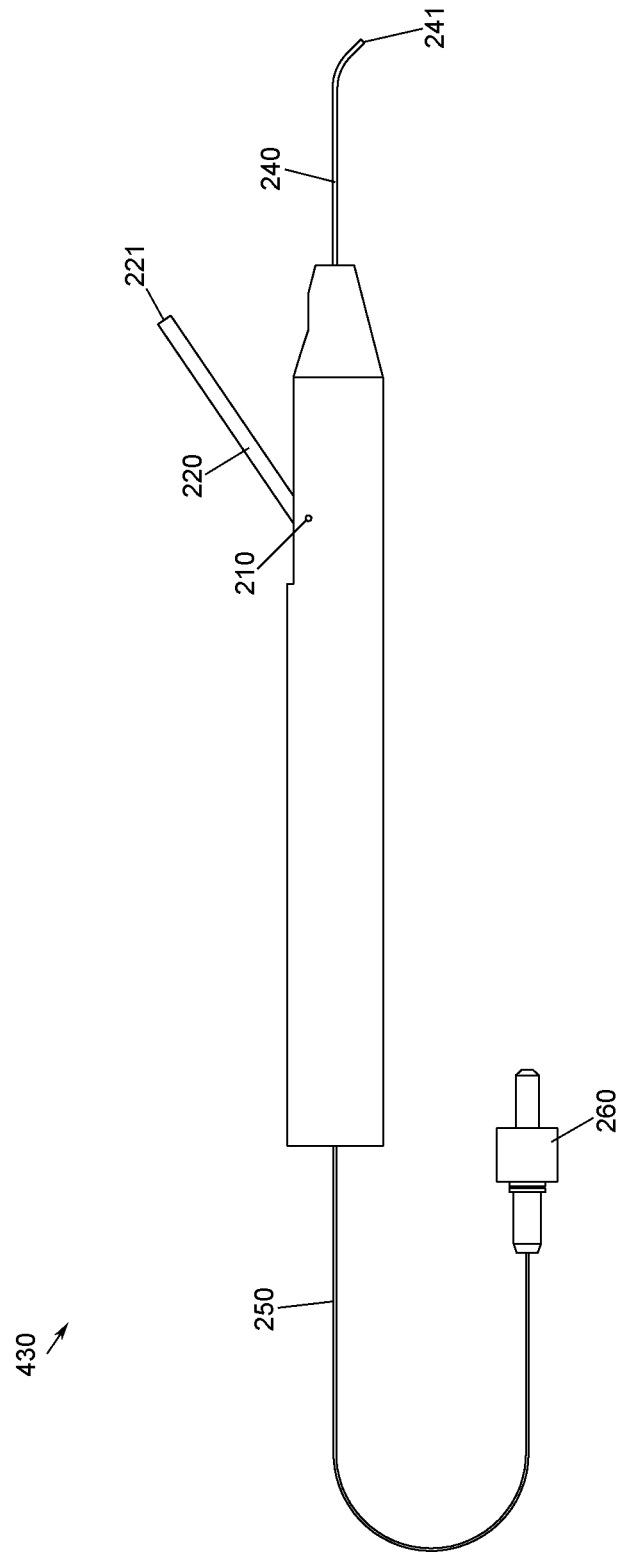

FIG. 4D illustrates an optic fiber in a third partially straightened position 430. In one or more embodiments, a rotation of actuation lever 220 about pivot pin 210 in a counter-clockwise direction may be configured to gradually straighten optic fiber 250 from an optic fiber in a second partially straightened position 420 to an optic fiber in a third partially straightened position 430. Illustratively, a reduction of a force applied to a portion of actuation lever 220 may be configured to rotate actuation lever distal end 221 about pivot pin 210 in a counter-clockwise direction. In one or more embodiments, a rotation of actuation lever distal end 221 about pivot pin 210 in a counter-clockwise direction may be configured to actuate optic fiber housing 230, e.g., towards handle distal end 101 and away from handle proximal end 102. Illustratively, an actuation of optic fiber housing 230 towards handle distal end 101 and away from handle proximal end 102 may be configured to extend optic fiber 250 relative to flexible housing tube 240. In one or more embodiments, an extension of optic fiber 250 relative to flexible housing tube 240 may be configured to reduce a compressive force applied to a portion of flexible housing tube 240. Illustratively, a reduction of a compressive force applied to a portion of flexible housing tube 240 may be configured to decompress a portion of flexible housing tube 240 causing flexible housing tube 240 to gradually straighten. In one or more embodiments, a gradual straightening of flexible housing tube 240 may be configured to gradually straighten optic fiber 250, e.g., from an optic fiber in a second partially straightened position 420 to an optic fiber in a third partially straightened position 430. Illustratively, a line tangent to optic fiber distal end 251 may intersect a line tangent to flexible housing tube proximal end 242 at a third partially straightened angle, e.g., when optic fiber 250 comprises an optic fiber in a third partially straightened position 430. In one or more embodiments, the third partially straightened angle may comprise any angle less than the second partially straightened angle. For example, the third partially straightened angle may comprise a 45 degree angle.

Figure 4E:
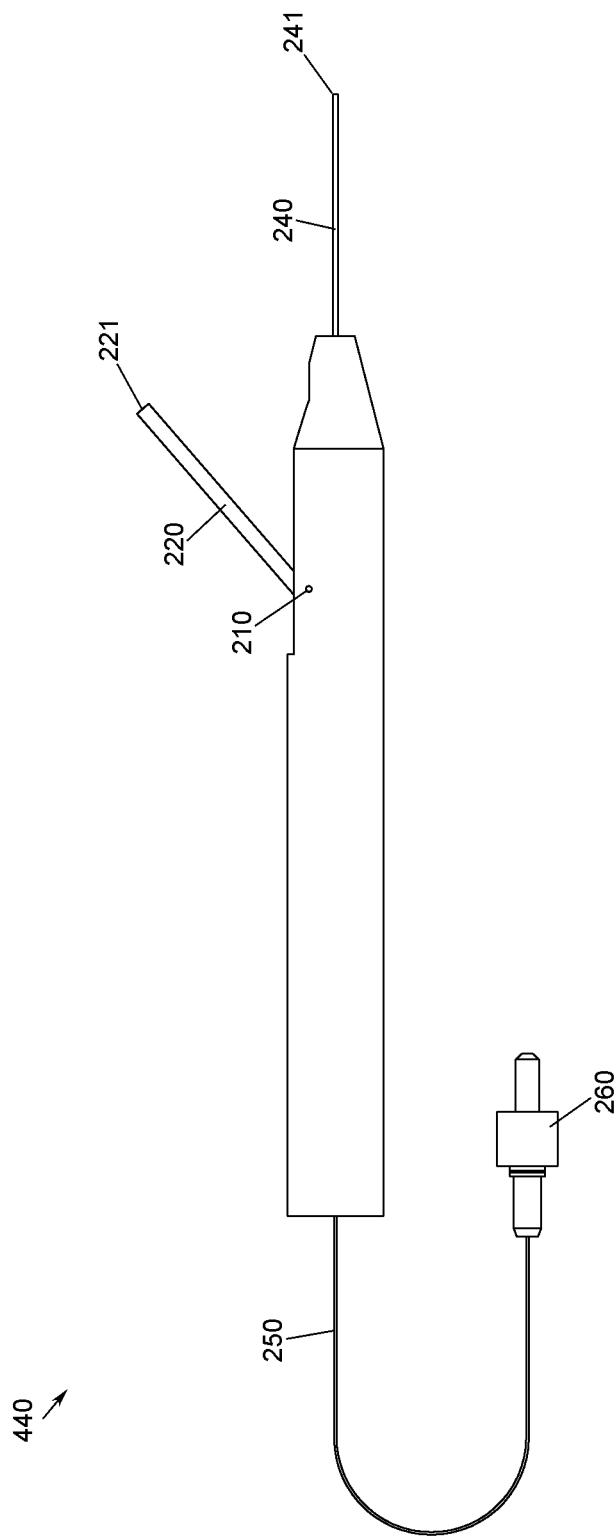

FIG. 4E illustrates an optic fiber in a fully straightened position 440. In one or more embodiments, a rotation of actuation lever 220 about pivot pin 210 in a counter-clockwise direction may be configured to gradually straighten optic fiber 250 from an optic fiber in a third partially straightened position 430 to an optic fiber in a fully straightened position 440. Illustratively, a reduction of a force applied to a portion of actuation lever 220 may be configured to rotate actuation lever distal end 221 about pivot pin 210 in a counter-clockwise direction. In one or more embodiments, a rotation of actuation lever distal end 221 about pivot pin 210 in a counter-clockwise direction may be configured to actuate optic fiber housing 230, e.g., towards handle distal end 101 and away from handle proximal end 102. Illustratively, an actuation of optic fiber housing 230 towards handle distal end 101 and away from handle proximal end 102 may be configured to extend optic fiber 250 relative to flexible housing tube 240. In one or more embodiments, an extension of optic fiber 250 relative to flexible housing tube 240 may be configured to reduce a compressive force applied to a portion of flexible housing tube 240. Illustratively, a reduction of a compressive force applied to a portion of flexible housing tube 240 may be configured to decompress a portion of flexible housing tube 240 causing flexible housing tube 240 to gradually straighten. In one or more embodiments, a gradual straightening of flexible housing tube 240 may be configured to gradually straighten optic fiber 250, e.g., from an optic fiber in a third partially straightened position 430 to an optic fiber in a fully straightened position 440. Illustratively, a line tangent to optic fiber distal end 251 may be parallel to a line tangent to flexible housing tube proximal end 242, e.g., when optic fiber 250 comprises an optic fiber in a fully straightened position 440.

Illustratively, a surgeon may aim optic fiber distal end 251 at any of a plurality of targets within an eye, e.g., to perform a photocoagulation procedure. In one or more embodiments, a surgeon may aim optic fiber distal end 251 at any target within a particular transverse plane of the inner eye by, e.g., rotating handle 100 to orient flexible housing tube 240 in an orientation configured to cause a curvature of flexible housing tube 240 within the particular transverse plane of the inner eye and varying a degree of rotation of actuation lever 220 about pivot pin 210. Illustratively, a surgeon may aim optic fiber distal end 251 at any target within a particular sagittal plane of the inner eye by, e.g., rotating handle 100 to orient flexible housing tube 240 in an orientation configured to cause a curvature of flexible housing tube 240 within the particular sagittal plane of the inner eye and varying a degree of rotation of actuation lever 220 about pivot pin 210. In one or more embodiments, a surgeon may aim optic fiber distal end 251 at any target within a particular frontal plane of the inner eye by, e.g., varying a degree of rotation of actuation lever 220 about pivot pin 210 to orient a line tangent to optic fiber distal end 251 wherein the line tangent to optic fiber distal end 251 is within the particular frontal plane of the inner eye and rotating handle 100. Illustratively, a surgeon may aim optic fiber distal end 251 at any target located outside of the particular transverse plane, the particular sagittal plane, and the particular frontal plane of the inner eye, e.g., by varying a rotational orientation of handle 100 and varying a degree of rotation of actuation lever 220 about pivot pin 210. In one or more embodiments, a surgeon may aim optic fiber distal end 251 at any target of a plurality of targets within an eye, e.g., without increasing a length of a portion of a steerable laser probe within the eye. Illustratively, a surgeon may aim optic fiber distal end 251 at any target of a plurality of targets within an eye, e.g., without decreasing a length of a portion of a steerable laser probe within the eye.

Figure 5:
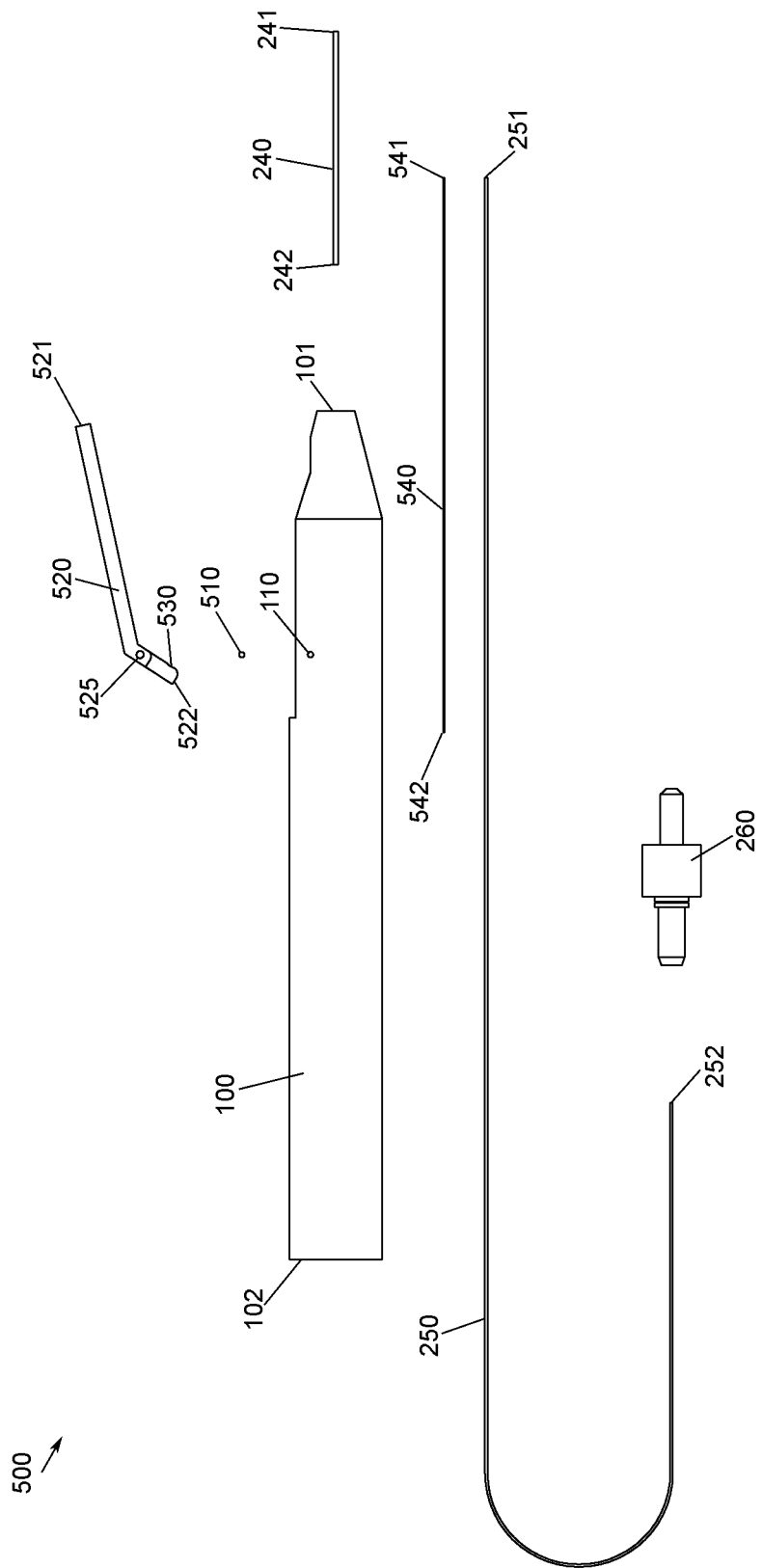
FIG. 5 is a schematic diagram illustrating an exploded view of a steerable laser probe assembly.

FIG. 5 is a schematic diagram illustrating an exploded view of a steerable laser probe assembly 500. In one or more embodiments, steerable laser probe assembly 500 may comprise a handle 100, a pivot pin 510, an actuation lever 520 having an actuation lever distal end 521 and an actuation lever proximal end 522, a cable 540 having a cable distal end 541 and a cable proximal end 542, a flexible housing tube 240 having a flexible housing tube distal end 241 and a flexible housing tube proximal end 242, an optic fiber 250 having an optic fiber distal end 251 and an optic fiber proximal end 252, and a light source interface 260. Illustratively, light source interface 260 may be configured to interface with optic fiber 250, e.g., at optic fiber proximal end 252. In one or more embodiments, light source interface 260 may comprise a standard light source connecter, e.g., an SMA connector.

Illustratively, a portion of flexible housing tube 240 may be fixed to handle distal end 101, e.g., flexible housing tube proximal end 242 may be fixed to handle distal end 101. In one or more embodiments, a portion of flexible housing tube 240 may be fixed to handle distal end 101, e.g., by an adhesive or any suitable fixation means. Illustratively, a portion of flexible housing tube 240 may be disposed within optic fiber guide 160, e.g., flexible housing tube proximal end 242 may be disposed within optic fiber guide 160. In one or more embodiments, a portion of flexible housing tube 240 may be fixed within optic fiber guide 160, e.g., by an adhesive or any suitable fixation means. Flexible housing tube 240 may be manufactured from any suitable material, e.g., polymers, metals, metal alloys, etc., or from any combination of suitable materials. Illustratively, flexible housing tube 240 may comprise a shape memory material, e.g., Nitinol. In one or more embodiments, flexible housing tube 240 may be manufactured from a material having an ultimate tensile strength between 700 and 1000 MPa. Illustratively, flexible housing tube 240 may be manufactured from a material having ultimate tensile strength less than 700 MPa or greater than 1000 MPa. In one or more embodiments, flexible housing tube 240 may be manufactured from a material having a modulus of elasticity between 30 and 80 GPa. Illustratively, flexible housing tube 240 may be manufactured from a material having a modulus of elasticity less than 30 GPa or greater than 80 GPa. In one or more embodiments, flexible housing tube 240 may be manufactured with dimensions suitable for performing microsurgical procedures, e.g., ophthalmic surgical procedures. Illustratively, flexible housing tube 240 may have an ultimate tensile strength between 1000 MPa and 1100 MPa. In one or more embodiments, flexible housing tube 240 may have an ultimate tensile strength less than 1000 MPa or greater than 1100 MPa.

Illustratively, a portion of actuation lever 520 may be disposed within actuation lever guide 150, e.g., actuation lever proximal end 522 may be disposed within actuation lever guide 150. In one or more embodiments, actuation lever 520 may comprise a pivot pin chamber 525 configured to enclose a portion of pivot pin 510. Illustratively, pivot pin 510 may be disposed within both pivot pin housing 110 and pivot pin chamber 525. In one or more embodiments, pivot pin 510 may be fixed within pivot pin housing 110. Illustratively, pivot pin 510 may be fixed within pivot pin housing 110, e.g., by an adhesive or any suitable fixation means. In one or more embodiments, pivot pin 510 may be configured to fix a portion of actuation lever 520 to handle 100, e.g., at pivot pin chamber 525. Illustratively, when pivot pin 510 is disposed within pivot pin chamber 525, pivot pin 510 may be configured to limit an actuation of actuation lever 520, e.g., to allow rotational actuation of actuation lever 520 about pivot pin 510. In one or more embodiments, actuation lever 520 may be configured to rotate about pivot pin 510, e.g., in response to an application of a force to a portion of actuation lever 520. Illustratively, pivot pin chamber 525 may be coated with a material, e.g., Teflon, configured to facilitate a rotation of actuation lever 520 about pivot pin 510.

In one or more embodiments, optic fiber 250 may be disposed within inner bore 140, actuation lever guide 150, optic fiber guide 160, and flexible housing tube 240. Illustratively, optic fiber 250 may be disposed within flexible housing tube 240 wherein optic fiber distal end 251 may be adjacent to flexible housing tube distal end 241. In one or more embodiments, a portion of optic fiber 250 may be fixed to an inner portion of flexible housing tube 240. Illustratively, a portion of optic fiber 250 may be fixed within flexible housing tube 240, e.g., by an adhesive or any suitable fixation means.

Illustratively, actuation lever 520 may comprise a cable housing 530 configured to house a portion of cable 540, e.g., cable proximal end 542. In one or more embodiments, cable 540 may be disposed within cable housing 530, actuation lever guide 150, optic fiber guide 160, and flexible housing tube 240. Illustratively, cable 540 may be disposed within flexible housing tube 240 wherein cable distal end 541 may be adjacent to flexible housing tube distal end 241. In one or more embodiments, a portion of cable 540 may be fixed to an inner portion of flexible housing tube 240. Illustratively, a portion of cable 540 may be fixed within flexible housing tube 240, e.g., by an adhesive or any suitable fixation means. In one or more embodiments, a portion of cable 540 may be fixed within cable housing 530, e.g., cable proximal end 542 may be disposed within cable housing 530. Illustratively, a portion of cable 540 may be fixed within cable housing 530, e.g., by an adhesive or any suitable fixation mechanism. In one or more embodiments, a portion of cable 540 may be fixed to an inner portion of flexible tube 240 and a portion of cable 540 may be fixed within cable housing 530.

In one or more embodiments, a surgeon may actuate actuation lever 520, e.g., by applying a force to a portion of actuation lever 520. Illustratively, an application of a force to actuation lever 520 may be configured to actuate actuation lever distal end 521 about pivot pin 510, e.g., in a clockwise direction. In one or more embodiments, an actuation of actuation lever distal end 521 about pivot pin 510 in a clockwise direction may be configured to actuate actuation lever proximal end 522 about pivot pin 510, e.g., in a clockwise direction. Illustratively, an actuation of actuation lever proximal end 522 about pivot pin 510 in a clockwise direction may be configured to actuate cable housing 530 within actuation lever guide 150, e.g., towards handle proximal end 102 and away from handle distal end 101. In one or more embodiments, an actuation of cable housing 530 towards handle proximal end 102 and away from handle distal end 101 may be configured to retract cable 540 relative to flexible housing tube 240. Illustratively, a retraction of cable 540 relative to flexible housing tube 240 may be configured to apply a force, e.g., a compressive force, to a portion of flexible housing tube 240. In one or more embodiments, an application of a force to a portion of flexible housing tube 240 may be configured to compress a portion of flexible housing tube 240. Illustratively, a compression of a portion of flexible housing tube 240 may be configured to cause flexible housing tube 240 to gradually curve. In one or more embodiments, a gradual curving of flexible housing tube 240 may be configured to gradually curve optic fiber 250. Illustratively, an actuation of actuation lever distal end 521 about pivot pin 510 in a clockwise direction may be configured to gradually curve optic fiber 250, e.g., an application of a force to a portion of actuation lever 520 may be configured to gradually curve optic fiber 250.

In one or more embodiments, a surgeon may actuate actuation lever 520, e.g., by reducing a force applied to a portion of actuation lever 520. Illustratively, a reduction of a force applied to actuation lever 520 may be configured to actuate actuation lever distal end 521 about pivot pin 510, e.g., in a counter-clockwise direction. In one or more embodiments, an actuation of actuation lever distal end 521 about pivot pin 510 in a counter-clockwise direction may be configured to actuate actuation lever proximal end 522 about pivot pin 510, e.g., in a counter-clockwise direction. Illustratively, an actuation of actuation lever proximal end 522 about pivot pin 510 in a counter-clockwise direction may be configured to actuate cable housing 530 within actuation lever guide 150, e.g., towards handle distal end 101 and away from handle proximal end 102. In one or more embodiments, an actuation of cable housing 530 towards handle distal end 101 and away from handle proximal end 102 may be configured to extend cable 540 relative to flexible housing tube 240. Illustratively, an extension of cable 540 relative to flexible housing tube 240 may be configured to reduce a force, e.g., a compressive force, applied to a portion of flexible housing tube 240. In one or more embodiments, a reduction of a force applied to a portion of flexible housing tube 240 may be configured to decompress a portion of flexible housing tube 240. Illustratively, a decompression of a portion of flexible housing tube 240 may be configured to cause flexible housing tube 240 to gradually straighten. In one or more embodiments, a gradual straightening of flexible housing tube 240 may be configured to gradually straighten optic fiber 250. Illustratively, an actuation of actuation lever distal end 521 about pivot pin 510 in a counter-clockwise direction may be configured to gradually straighten optic fiber 250, e.g., a reduction of a force applied to a portion of actuation lever 520 may be configured to gradually straighten optic fiber 250.

Figure 6A:
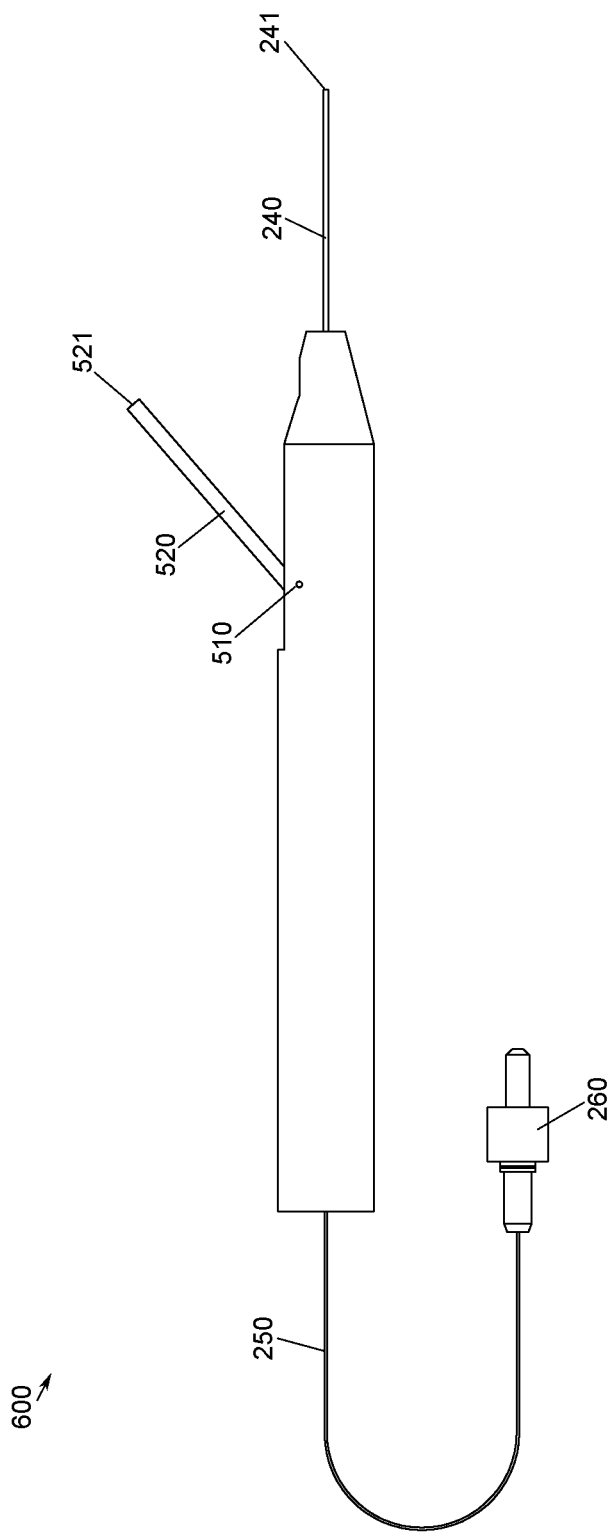
FIGS. 6A, 6B, 6C, 6D, and 6E illustrate a gradual curving of an optic fiber.

FIGS. 6A, 6B, 6C, 6D, and 6E illustrate a gradual curving of an optic fiber 250. FIG. 6A illustrates a straight optic fiber 600. In one or more embodiments, optic fiber 250 may comprise a straight optic fiber 600, e.g., when cable 540 is fully extended relative to flexible housing tube 240. For example, optic fiber 250 may comprise a straight optic fiber 600 when cable housing 530 is fully extended relative to flexible housing tube 240. Illustratively, optic fiber 250 may comprise a straight optic fiber 600, e.g., when a portion of flexible housing tube 240 is fully decompressed. In one or more embodiments, optic fiber 250 may comprise a straight optic fiber 600, e.g., when no force is applied to actuation lever 520. Illustratively, a line tangent to optic fiber distal end 251 may be parallel to a line tangent to flexible housing tube proximal end 242, e.g., when optic fiber 250 comprises a straight optic fiber 600.

Figure 6B:
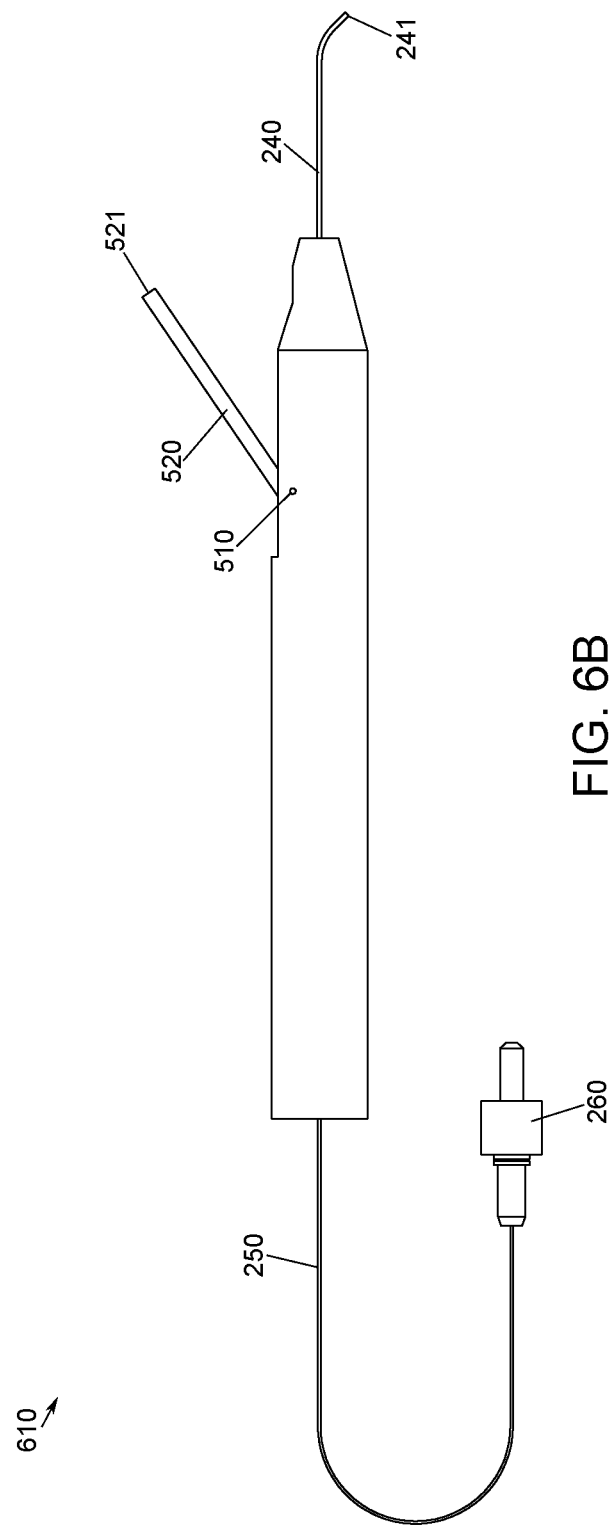

FIG. 6B illustrates an optic fiber in a first curved position 610. In one or more embodiments, a rotation of actuation lever 520 about pivot pin 510 in a clockwise direction may be configured to gradually curve optic fiber 250 from a straight optic fiber 600 to an optic fiber in a first curved position 610. Illustratively, an application of a force to a portion of actuation lever 520 may be configured to rotate actuation lever distal end 521 about pivot pin 510 in a clockwise direction. In one or more embodiments, a rotation of actuation lever distal end 521 about pivot pin 510 in a clockwise direction may be configured to actuate cable housing 530, e.g., towards handle proximal end 102 and away from handle distal end 101. Illustratively, an actuation of cable housing 530 towards handle proximal end 102 and away from handle distal end 101 may be configured to retract cable 540 relative to flexible housing tube 240. In one or more embodiments, a retraction of cable 540 relative to flexible housing tube 240 may be configured to apply a compressive force to a portion of flexible housing tube 240. Illustratively, an application of a compressive force to a portion of flexible housing tube 240 may be configured to compress a portion of flexible housing tube 240 causing flexible housing tube 240 to gradually curve. In one or more embodiments, a gradual curving of flexible housing tube 240 may be configured to gradually curve optic fiber 250, e.g., from a straight optic fiber 600 to an optic fiber in a first curved position 610. Illustratively, a line tangent to optic fiber distal end 251 may intersect a line tangent to flexible housing tube proximal end 242 at a first angle, e.g., when optic fiber 250 comprises an optic fiber in a first curved position 610. In one or more embodiments, the first angle may comprise any angle greater than zero degrees. For example, the first angle may comprise a 45 degree angle.

Figure 6C:
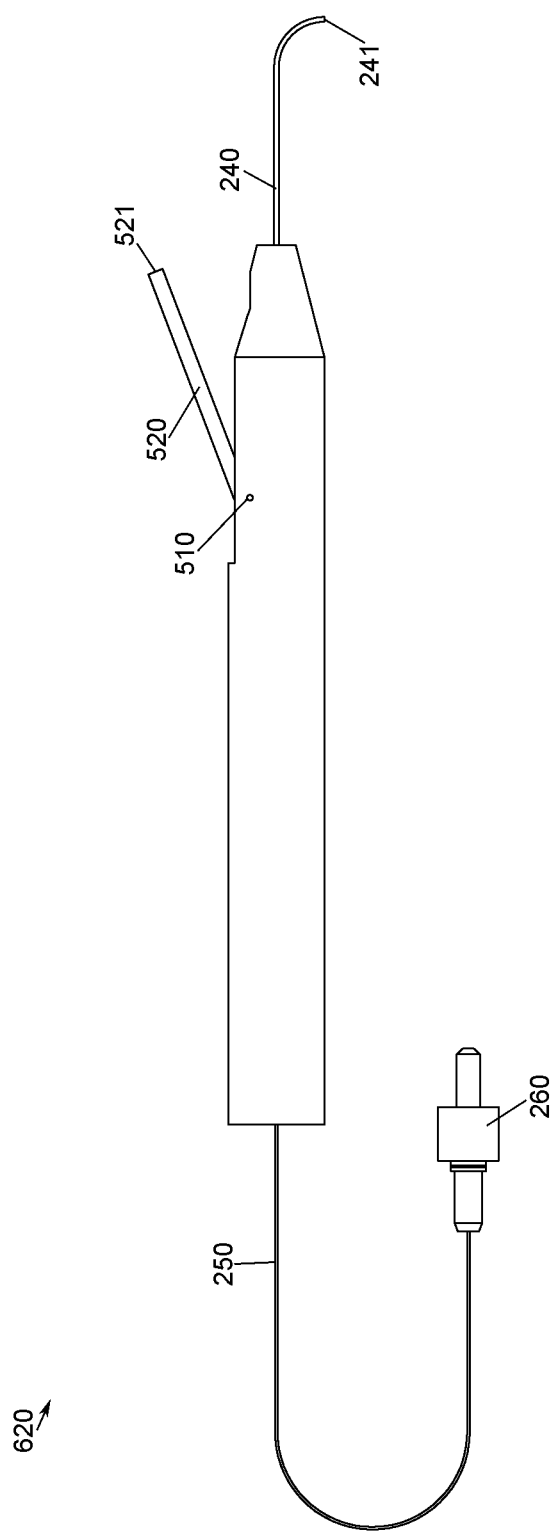

FIG. 6C illustrates an optic fiber in a second curved position 620. In one or more embodiments, a rotation of actuation lever 520 about pivot pin 510 in a clockwise direction may be configured to gradually curve optic fiber 250 from an optic fiber in a first curved position 610 to an optic fiber in a second curved position 620. Illustratively, an application of a force to a portion of actuation lever 520 may be configured to rotate actuation lever distal end 521 about pivot pin 510 in a clockwise direction. In one or more embodiments, a rotation of actuation lever distal end 521 about pivot pin 510 in a clockwise direction may be configured to actuate cable housing 530, e.g., towards handle proximal end 102 and away from handle distal end 101. Illustratively, an actuation of cable housing 530 towards handle proximal end 102 and away from handle distal end 101 may be configured to retract cable 540 relative to flexible housing tube 240. In one or more embodiments, a retraction of cable 540 relative to flexible housing tube 240 may be configured to apply a compressive force to a portion of flexible housing tube 240. Illustratively, an application of a compressive force to a portion of flexible housing tube 240 may be configured to compress a portion of flexible housing tube 240 causing flexible housing tube 240 to gradually curve. In one or more embodiments, a gradual curving of flexible housing tube 240 may be configured to gradually curve optic fiber 250, e.g., from an optic fiber in a first curved position 610 to an optic fiber in a second curved position 620. Illustratively, a line tangent to optic fiber distal end 251 may intersect a line tangent to flexible housing tube proximal end 242 at a second angle, e.g., when optic fiber 250 comprises an optic fiber in a second curved position 620. In one or more embodiments, the second angle may comprise any angle greater than the first angle. For example, the second angle may comprise a 90 degree angle.

Figure 6D:
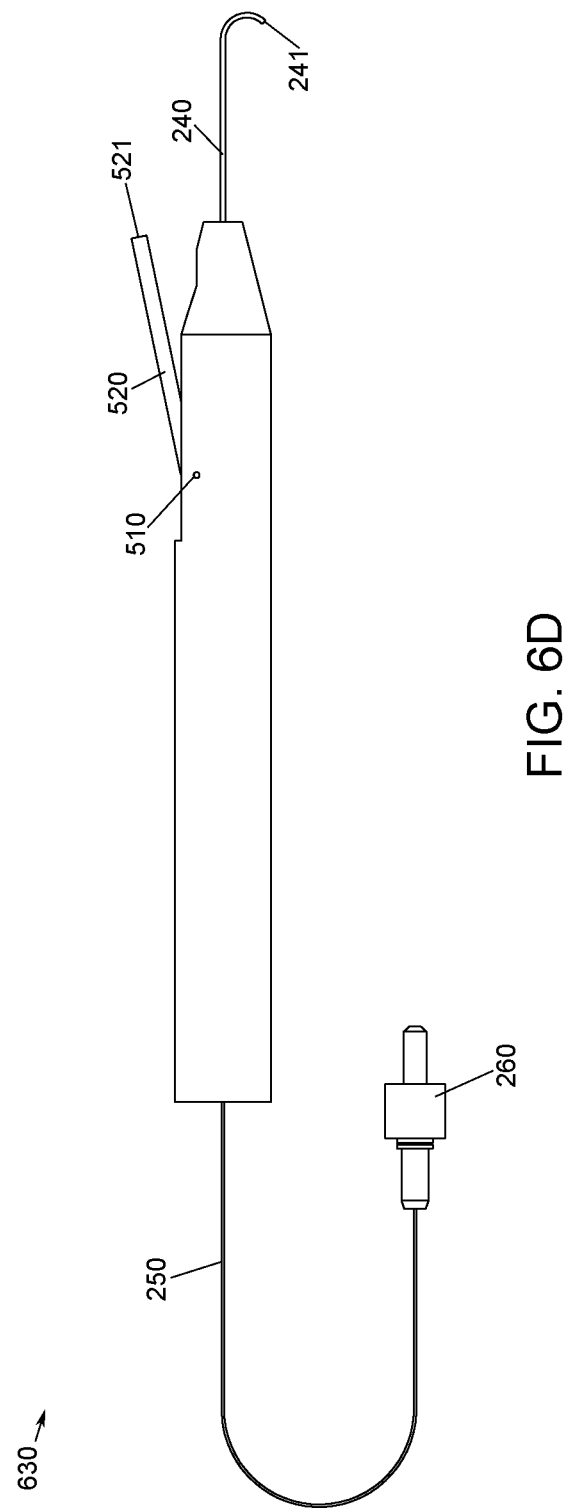

FIG. 6D illustrates an optic fiber in a third curved position 630. In one or more embodiments, a rotation of actuation lever 520 about pivot pin 510 in a clockwise direction may be configured to gradually curve optic fiber 250 from an optic fiber in a second curved position 620 to an optic fiber in a third curved position 630. Illustratively, an application of a force to a portion of actuation lever 520 may be configured to rotate actuation lever distal end 521 about pivot pin 510 in a clockwise direction. In one or more embodiments, a rotation of actuation lever distal end 521 about pivot pin 510 in a clockwise direction may be configured to actuate cable housing 530, e.g., towards handle proximal end 102 and away from handle distal end 101. Illustratively, an actuation of cable housing 530 towards handle proximal end 102 and away from handle distal end 101 may be configured to retract cable 540 relative to flexible housing tube 240. In one or more embodiments, a retraction of cable 540 relative to flexible housing tube 240 may be configured to apply a compressive force to a portion of flexible housing tube 240. Illustratively, an application of a compressive force to a portion of flexible housing tube 240 may be configured to compress a portion of flexible housing tube 240 causing flexible housing tube 240 to gradually curve. In one or more embodiments, a gradual curving of flexible housing tube 240 may be configured to gradually curve optic fiber 250, e.g., from an optic fiber in a second curved position 620 to an optic fiber in a third curved position 630. Illustratively, a line tangent to optic fiber distal end 251 may intersect a line tangent to flexible housing tube proximal end 242 at a third angle, e.g., when optic fiber 250 comprises an optic fiber in a third curved position 630. In one or more embodiments, the third angle may comprise any angle greater than the second angle. For example, the third angle may comprise a 135 degree angle.

Figure 6E:
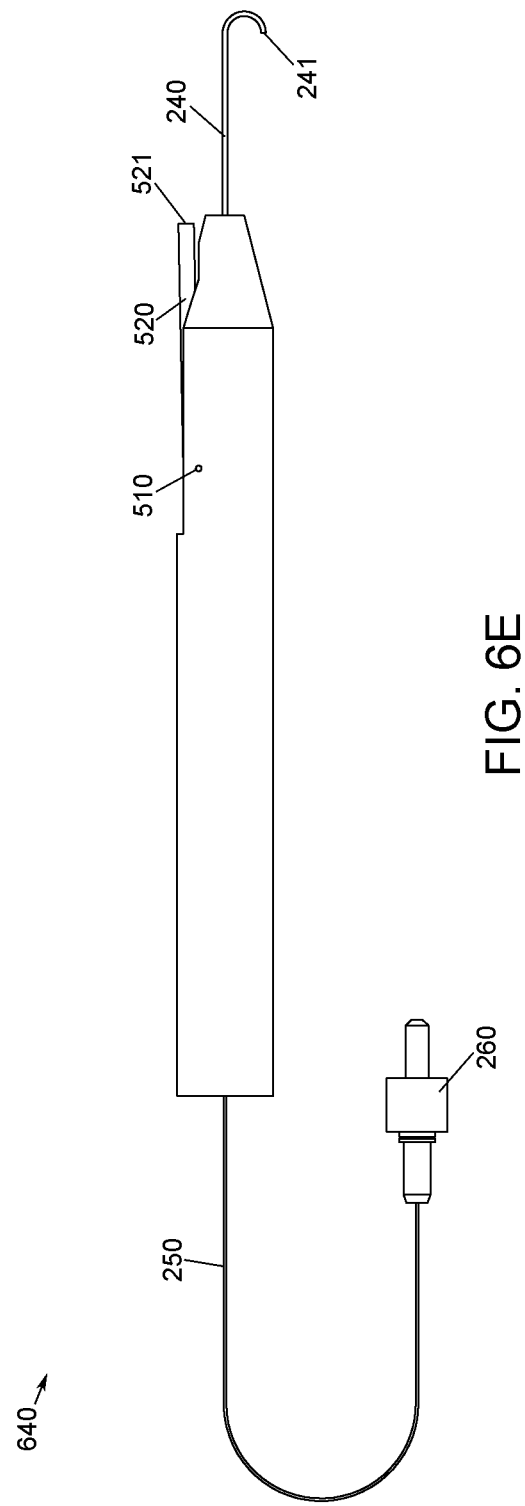

FIG. 6E illustrates an optic fiber in a fourth curved position 640. In one or more embodiments, a rotation of actuation lever 520 about pivot pin 510 in a clockwise direction may be configured to gradually curve optic fiber 250 from an optic fiber in a third curved position 630 to an optic fiber in a fourth curved position 640. Illustratively, an application of a force to a portion of actuation lever 520 may be configured to rotate actuation lever distal end 521 about pivot pin 510 in a clockwise direction. In one or more embodiments, a rotation of actuation lever distal end 521 about pivot pin 510 in a clockwise direction may be configured to actuate cable housing 530, e.g., towards handle proximal end 102 and away from handle distal end 101. Illustratively, an actuation of cable housing 530 towards handle proximal end 102 and away from handle distal end 101 may be configured to retract cable 540 relative to flexible housing tube 240. In one or more embodiments, a retraction of cable 540 relative to flexible housing tube 240 may be configured to apply a compressive force to a portion of flexible housing tube 240. Illustratively, an application of a compressive force to a portion of flexible housing tube 240 may be configured to compress a portion of flexible housing tube 240 causing flexible housing tube 240 to gradually curve. In one or more embodiments, a gradual curving of flexible housing tube 240 may be configured to gradually curve optic fiber 250, e.g., from an optic fiber in a third curved position 630 to an optic fiber in a fourth curved position 640. Illustratively, a line tangent to optic fiber distal end 251 may be parallel to a line tangent to flexible housing tube proximal end 242, e.g., when optic fiber 250 comprises an optic fiber in a fourth curved position 640.

In one or more embodiments, one or more properties of a steerable laser probe may be adjusted to attain one or more desired steerable laser probe features. For example, a length that flexible housing tube distal end 241 extends from handle distal end 101 may be adjusted to vary a degree of rotation of actuation lever 520 configured to curve flexible housing tube 240 to a particular curved position. In one or more embodiments, a stiffness of flexible housing tube 240 may be adjusted to vary a degree of rotation of actuation lever 520 configured to curve flexible housing tube 240 to a particular curved position. Illustratively, a material comprising flexible housing tube 240 may be adjusted to vary a degree of rotation of actuation lever 520 configured to curve flexible housing tube 240 to a particular curved position.

Illustratively, a position of pivot pin 510 may be adjusted to vary a degree of rotation of actuation lever 520 configured to curve flexible housing tube 240 to a particular curved position. In one or more embodiments, a geometry of actuation lever 520 may be adjusted to vary a degree of rotation of actuation lever 520 configured to curve flexible housing tube 240 to a particular curved position. Illustratively, one or more locations within flexible housing tube 240 wherein cable 540 may be fixed to an inner portion of flexible housing tube 240 may be adjusted to vary a degree of rotation of actuation lever 520 configured to curve flexible housing tube 240 to a particular curved position.

In one or more embodiments, a mechanism configured to control a gradual curving of optic fiber 250 or a gradual straightening of optic fiber 250 may be varied to, e.g., attain one or more desired steerable laser probe features. Illustratively, a mechanism configured to control a gradual curving of optic fiber 250 may or may not be configured to control a gradual straightening of optic fiber 250. In one or more embodiments, a mechanism configured to control a gradual straightening of optic fiber 250 may or may not be configured to control a gradual curving of optic fiber 250. Illustratively, a steerable laser probe may be modified to allow a surgeon to selectively fix optic fiber 250 in a particular curved position. In one or more embodiments, a detent or a pawl may be added to a steerable laser probe, e.g., to temporarily fix actuation lever 520 in a position relative to handle proximal end 102. Illustratively, one or more magnets may be added to a steerable laser probe, e.g., to temporarily fix actuation lever 520 in a position relative to handle proximal end 102. In one or more embodiments, a switch or any other suitable control mechanism may be added to a steerable laser probe to control a gradual curving of optic fiber 250 or a gradual straightening of optic fiber 250.

In one or more embodiments, at least a portion of optic fiber 250 may be enclosed in an optic fiber sleeve configured to, e.g., protect optic fiber 250, vary a stiffness of optic fiber 250, vary an optical property of optic fiber 250, etc. Illustratively, an optic fiber sleeve may be configured to compress a first portion of flexible housing tube 240 and cable 540 may be configured to compress a second portion of flexible housing tube 240. For example, an optic fiber sleeve may enclose a portion of optic fiber 250 and the optic fiber sleeve may be fixed within cable housing 530 and also fixed to a portion of flexible housing tube 240. In one or more embodiments, a rotation of actuation lever 520 about pivot pin 510 in a clockwise direction may be configured to retract an optic fiber sleeve relative to flexible housing tube 240. Illustratively, a retraction of an optic fiber sleeve relative to flexible housing tube 240 may be configured to cause the optic fiber sleeve to apply a force, e.g., a compressive force, to a portion of flexible housing tube 240. In one or more embodiments, an application of a force to a portion of flexible housing tube 240 may be configured to compress a portion of flexible housing tube 240 causing flexible housing tube 240 to gradually curve.

Figure 7B:
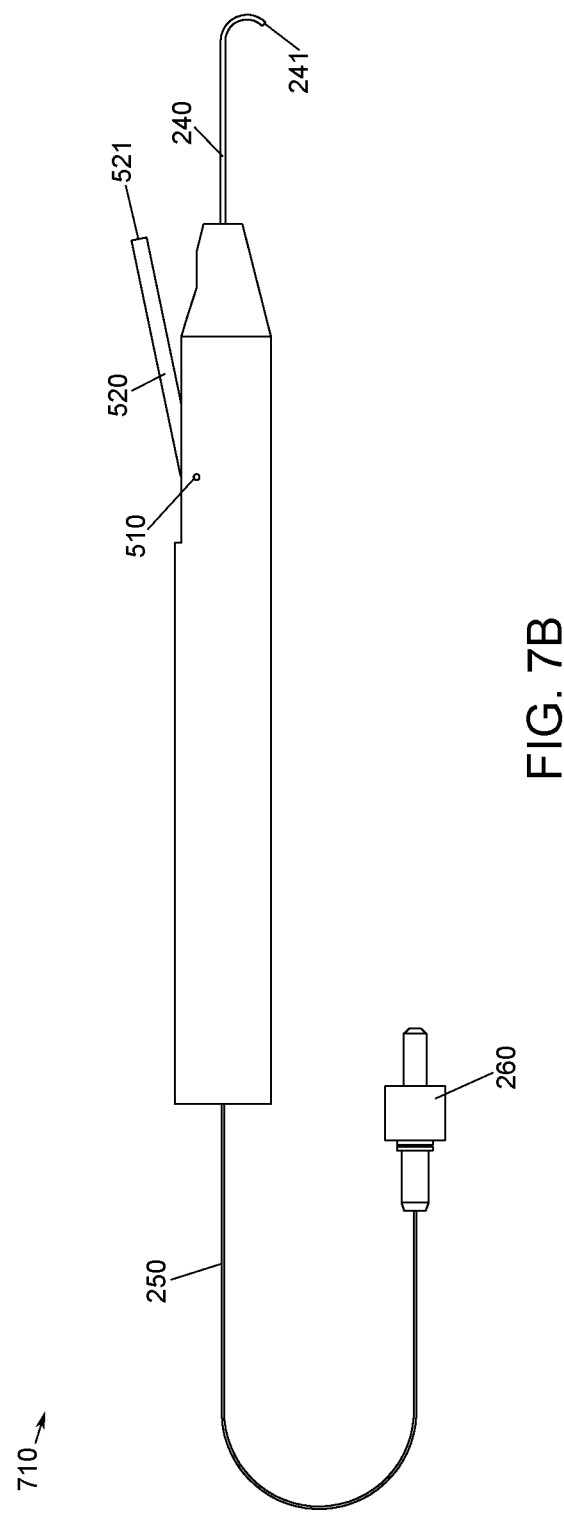

FIGS. 7A, 7B, 7C, 7D, and 7E illustrate a gradual straightening of an optic fiber 250. FIG. 7A illustrates a fully curved optic fiber 700. In one or more embodiments, optic fiber 250 may comprise a fully curved optic fiber 700, e.g., when cable 540 is fully retracted relative to flexible housing tube 240. For example, optic fiber 250 may comprise a fully curved optic fiber 700 when cable housing 530 is fully retracted relative to flexible housing tube 240. Illustratively, optic fiber 250 may comprise a fully curved optic fiber 700, e.g., when a portion of flexible housing tube 240 is compressed. In one or more embodiments, optic fiber 250 may comprise a fully curved optic fiber 700, e.g., when a force is applied to actuation lever 520. Illustratively, a line tangent to optic fiber distal end 251 may be parallel to a line tangent to flexible housing tube proximal end 242, e.g., when optic fiber 250 comprises a fully curved optic fiber 700.

FIG. 7B illustrates an optic fiber in a first partially straightened position 710. In one or more embodiments, a rotation of actuation lever 520 about pivot pin 510 in a counter-clockwise direction may be configured to gradually straighten optic fiber 250 from a fully curved optic fiber 700 to an optic fiber in a first partially straightened position 710. Illustratively, a reduction of a force applied to a portion of actuation lever 520 may be configured to rotate actuation lever distal end 521 about pivot pin 510 in a counter-clockwise direction. In one or more embodiments, a rotation of actuation lever distal end 521 about pivot pin 510 in a counter-clockwise direction may be configured to actuate cable housing 530, e.g., towards handle distal end 101 and away from handle proximal end 102. Illustratively, an actuation of cable housing 530 towards handle distal end 101 and away from handle proximal end 102 may be configured to extend cable 540 relative to flexible housing tube 240. In one or more embodiments, an extension of cable 540 relative to flexible housing tube 240 may be configured to reduce a compressive force applied to a portion of flexible housing tube 240. Illustratively, a reduction of a compressive force applied to a portion of flexible housing tube 240 may be configured to decompress a portion of flexible housing tube 240 causing flexible housing tube 240 to gradually straighten. In one or more embodiments, a gradual straightening of flexible housing tube 240 may be configured to gradually straighten optic fiber 250, e.g., from a fully curved optic fiber 700 to an optic fiber in a first partially straightened position 710. Illustratively, a line tangent to optic fiber distal end 251 may intersect a line tangent to flexible housing tube proximal end 242 at a first partially straightened angle, e.g., when optic fiber 250 comprises an optic fiber in a first partially straightened position 710. In one or more embodiments, the first partially straightened angle may comprise any angle less than 180 degrees. For example, the first partially straightened angle may comprise a 135 degree angle.

Figure 7C:
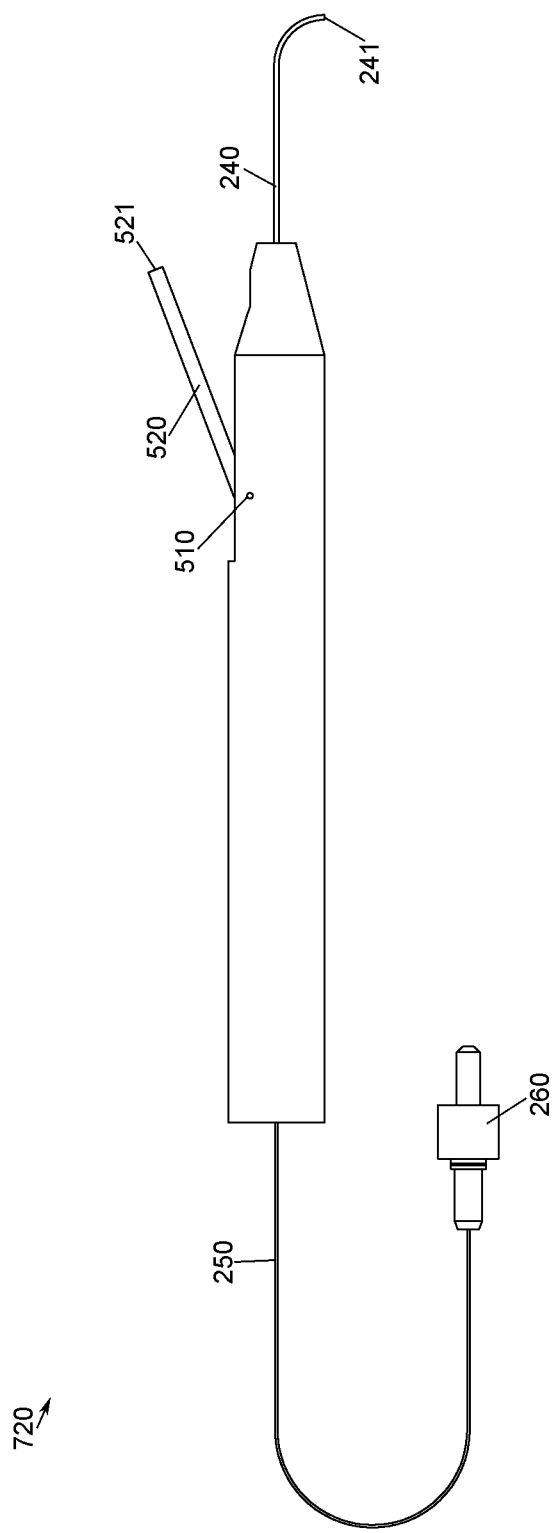

FIG. 7C illustrates an optic fiber in a second partially straightened position 720. In one or more embodiments, a rotation of actuation lever 520 about pivot pin 510 in a counter-clockwise direction may be configured to gradually straighten optic fiber 250 from an optic fiber in a first partially straightened position 710 to an optic fiber in a second partially straightened position 720. Illustratively, a reduction of a force applied to a portion of actuation lever 520 may be configured to rotate actuation lever distal end 521 about pivot pin 510 in a counter-clockwise direction. In one or more embodiments, a rotation of actuation lever distal end 521 about pivot pin 510 in a counter-clockwise direction may be configured to actuate cable housing 530, e.g., towards handle distal end 101 and away from handle proximal end 102. Illustratively, an actuation of cable housing 530 towards handle distal end 101 and away from handle proximal end 102 may be configured to extend cable 540 relative to flexible housing tube 240. In one or more embodiments, an extension of cable 540 relative to flexible housing tube 240 may be configured to reduce a compressive force applied to a portion of flexible housing tube 240. Illustratively, a reduction of a compressive force applied to a portion of flexible housing tube 240 may be configured to decompress a portion of flexible housing tube 240 causing flexible housing tube 240 to gradually straighten. In one or more embodiments, a gradual straightening of flexible housing tube 240 may be configured to gradually straighten optic fiber 250, e.g., from an optic fiber in a first partially straightened position 710 to an optic fiber in a second partially straightened position 720. Illustratively, a line tangent to optic fiber distal end 251 may intersect a line tangent to flexible housing tube proximal end 242 at a second partially straightened angle, e.g., when optic fiber 250 comprises an optic fiber in a second partially straightened position 720. In one or more embodiments, the second partially straightened angle may comprise any angle less than the first partially straightened angle. For example, the second partially straightened angle may comprise a 90 degree angle.

Figure 7D:
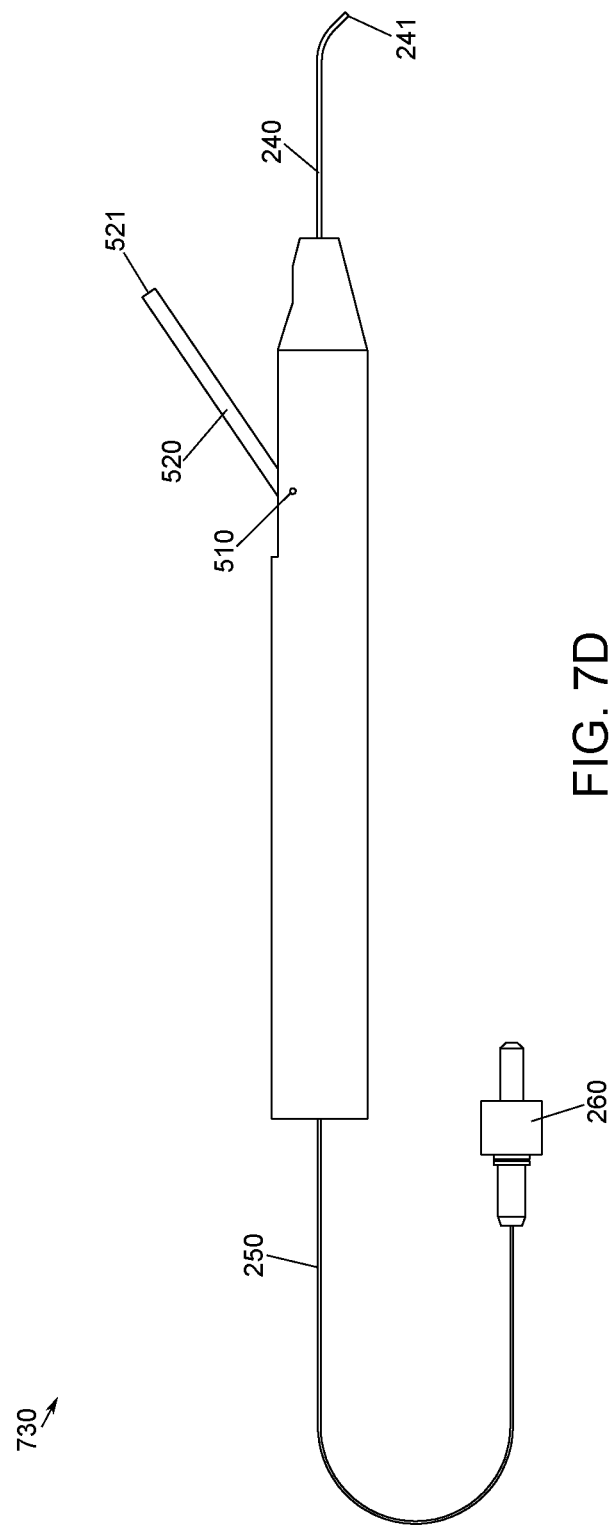

FIG. 7D illustrates an optic fiber in a third partially straightened position 730. In one or more embodiments, a rotation of actuation lever 520 about pivot pin 510 in a counter-clockwise direction may be configured to gradually straighten optic fiber 250 from an optic fiber in a second partially straightened position 720 to an optic fiber in a third partially straightened position 730. Illustratively, a reduction of a force applied to a portion of actuation lever 520 may be configured to rotate actuation lever distal end 521 about pivot pin 510 in a counter-clockwise direction. In one or more embodiments, a rotation of actuation lever distal end 521 about pivot pin 510 in a counter-clockwise direction may be configured to actuate cable housing 530, e.g., towards handle distal end 101 and away from handle proximal end 102. Illustratively, an actuation of cable housing 530 towards handle distal end 101 and away from handle proximal end 102 may be configured to extend cable 540 relative to flexible housing tube 240. In one or more embodiments, an extension of cable 540 relative to flexible housing tube 240 may be configured to reduce a compressive force applied to a portion of flexible housing tube 240. Illustratively, a reduction of a compressive force applied to a portion of flexible housing tube 240 may be configured to decompress a portion of flexible housing tube 240 causing flexible housing tube 240 to gradually straighten. In one or more embodiments, a gradual straightening of flexible housing tube 240 may be configured to gradually straighten optic fiber 250, e.g., from an optic fiber in a second partially straightened position 720 to an optic fiber in a third partially straightened position 730. Illustratively, a line tangent to optic fiber distal end 251 may intersect a line tangent to flexible housing tube proximal end 242 at a third partially straightened angle, e.g., when optic fiber 250 comprises an optic fiber in a third partially straightened position 730. In one or more embodiments, the third partially straightened angle may comprise any angle less than the second partially straightened angle. For example, the third partially straightened angle may comprise a 45 degree angle.

Figure 7E:
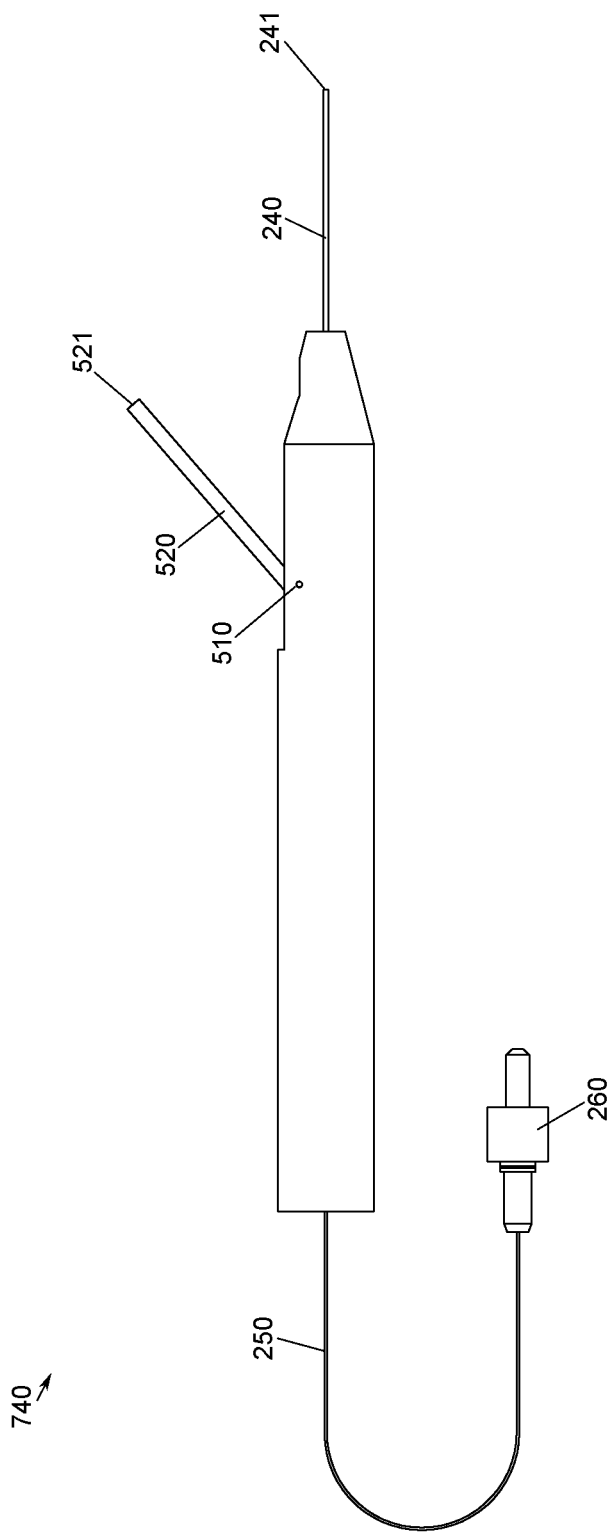

FIG. 7E illustrates an optic fiber in a fully straightened position 740. In one or more embodiments, a rotation of actuation lever 520 about pivot pin 510 in a counter-clockwise direction may be configured to gradually straighten optic fiber 250 from an optic fiber in a third partially straightened position 730 to an optic fiber in a fully straightened position 740. Illustratively, a reduction of a force applied to a portion of actuation lever 520 may be configured to rotate actuation lever distal end 521 about pivot pin 510 in a counter-clockwise direction. In one or more embodiments, a rotation of actuation lever distal end 521 about pivot pin 510 in a counter-clockwise direction may be configured to actuate cable housing 530, e.g., towards handle distal end 101 and away from handle proximal end 102. Illustratively, an actuation of cable housing 530 towards handle distal end 101 and away from handle proximal end 102 may be configured to extend cable 540 relative to flexible housing tube 240. In one or more embodiments, an extension of cable 540 relative to flexible housing tube 240 may be configured to reduce a compressive force applied to a portion of flexible housing tube 240. Illustratively, a reduction of a compressive force applied to a portion of flexible housing tube 240 may be configured to decompress a portion of flexible housing tube 240 causing flexible housing tube 240 to gradually straighten. In one or more embodiments, a gradual straightening of flexible housing tube 240 may be configured to gradually straighten optic fiber 250, e.g., from an optic fiber in a third partially straightened position 730 to an optic fiber in a fully straightened position 740. Illustratively, a line tangent to optic fiber distal end 251 may be parallel to a line tangent to flexible housing tube proximal end 242, e.g., when optic fiber 250 comprises an optic fiber in a fully straightened position 740.

Illustratively, a surgeon may aim optic fiber distal end 251 at any of a plurality of targets within an eye, e.g., to perform a photocoagulation procedure. In one or more embodiments, a surgeon may aim optic fiber distal end 251 at any target within a particular transverse plane of the inner eye by, e.g., rotating handle 100 to orient flexible housing tube 240 in an orientation configured to cause a curvature of flexible housing tube 240 within the particular transverse plane of the inner eye and varying a degree of rotation of actuation lever 520 about pivot pin 510. Illustratively, a surgeon may aim optic fiber distal end 251 at any target within a particular sagittal plane of the inner eye by, e.g., rotating handle 100 to orient flexible housing tube 240 in an orientation configured to cause a curvature of flexible housing tube 240 within the particular sagittal plane of the inner eye and varying a degree of rotation of actuation lever 520 about pivot pin 510. In one or more embodiments, a surgeon may aim optic fiber distal end 251 at any target within a particular frontal plane of the inner eye by, e.g., varying a degree of rotation of actuation lever 520 about pivot pin 510 to orient a line tangent to optic fiber distal end 251 wherein the line tangent to optic fiber distal end 251 is within the particular frontal plane of the inner eye and rotating handle 100. Illustratively, a surgeon may aim optic fiber distal end 251 at any target located outside of the particular transverse plane, the particular sagittal plane, and the particular frontal plane of the inner eye, e.g., by varying a rotational orientation of handle 100 and varying a degree of rotation of actuation lever 520 about pivot pin 510. In one or more embodiments, a surgeon may aim optic fiber distal end 251 at any target of a plurality of targets within an eye, e.g., without increasing a length of a portion of a steerable laser probe within the eye. Illustratively, a surgeon may aim optic fiber distal end 251 at any target of a plurality of targets within an eye, e.g., without decreasing a length of a portion of a steerable laser probe within the eye.

The foregoing description has been directed to particular embodiments of this invention. It will be apparent; however, that other variations and modifications may be made to the described embodiments, with the attainment of some or all of their advantages. Specifically, it should be noted that the principles of the present invention may be implemented in any probe system. Furthermore, while this description has been written in terms of a steerable laser probe, the teachings of the present invention are equally suitable to systems where the functionality of actuation may be employed. Therefore, it is the object of the appended claims to cover all such variations and modifications as come within the true spirit and scope of the invention.

What is claimed is:

1. A method of operating a steerable laser probe, comprising:
    reducing a force applied to a portion of an actuation lever of a handle of the steerable laser probe wherein the handle has a handle distal end and a handle proximal end and wherein the actuation lever has an actuation lever distal end and an actuation lever proximal end;
    limiting an actuation of the actuation lever by a pivot pin wherein the pivot pin is disposed in a pivot pin housing of the handle and a pivot pin chamber of the actuation lever;
    actuating the actuation lever in an actuation lever channel of the handle;
    actuating the actuation lever proximal end towards the handle distal end and away from the handle proximal end wherein the actuation lever proximal end is disposed in an actuation lever guide and wherein the actuation lever distal end is not disposed in the actuation lever guide;
    actuating an optic fiber housing of the actuation lever within the actuation lever guide towards the handle distal end and away from the handle proximal end in association with an optic fiber having an optic fiber distal end and an optic fiber proximal end;
    straightening a flexible housing tube having a flexible housing tube distal end and a flexible housing tube proximal end wherein the flexible housing tube proximal end is disposed in an optic fiber guide of the handle and wherein the flexible housing tube proximal end is fixed in the optic fiber guide; and
    straightening the optic fiber wherein the optic fiber is disposed in the actuation lever guide, the optic fiber housing, the optic fiber guide, and the flexible housing tube wherein the optic fiber distal end is adjacent to the flexible housing tube distal end and wherein a first portion of the optic fiber is fixed to an inner portion of the flexible housing tube and wherein a second portion of the optic fiber is fixed in the optic fiber housing.

2. The method of claim 1 further comprising:
    extending the optic fiber relative to the flexible housing tube.

3. The method of claim 1 further comprising:
    aiming the optic fiber distal end at a surgical target in an eye.

4. The method of claim 1 further comprising:
    straightening the optic fiber 45 degrees relative to the flexible housing tube proximal end.

5. The method of claim 1 further comprising: straightening the optic fiber 90 degrees relative to the flexible housing tube proximal end.

* * * * *